(12) United States Patent
Mullen et al.

(10) Patent No.: US 11,037,045 B2
(45) Date of Patent: Jun. 15, 2021

(54) CARDS AND DEVICES WITH MAGNETIC EMULATORS WITH ZONING CONTROL AND ADVANCED INTERIORS

(71) Applicant: Dynamics Inc., Cheswick, PA (US)

(72) Inventors: Jeffrey D. Mullen, Glenshaw, PA (US); David Lambeth, Pittsburgh, PA (US); Bruce Cloutier, Jeannette, PA (US)

(73) Assignee: DYNAMICS INC., Pittsburgh, PA (US)

( * ) Notice: Subject to any disclaimer, the term of this patent is extended or adjusted under 35 U.S.C. 154(b) by 0 days.

(21) Appl. No.: 16/244,080

(22) Filed: Jan. 9, 2019

(65) Prior Publication Data

US 2019/0197387 A1    Jun. 27, 2019

Related U.S. Application Data

(63) Continuation of application No. 15/583,356, filed on May 1, 2017, which is a continuation of application
(Continued)

(51) Int. Cl.
*G06K 19/08* (2006.01)
*G06K 19/07* (2006.01)
(Continued)

(52) U.S. Cl.
CPC ......... *G06K 19/083* (2013.01); *G06F 3/0488* (2013.01); *G06K 7/0004* (2013.01); *G06K 7/084* (2013.01); *G06K 7/087* (2013.01); *G06K 7/10297* (2013.01); *G06K 19/06187* (2013.01); *G06K 19/06206* (2013.01); *G06K 19/07* (2013.01); *G06K 19/0702* (2013.01);
(Continued)

(58) Field of Classification Search
CPC .................................................. G06K 19/083
USPC .................... 235/449, 492, 493, 380, 382.5
See application file for complete search history.

(56) References Cited

U.S. PATENT DOCUMENTS

| 4,353,064 A | 10/1982 | Stamm |
| 4,394,654 A | 7/1983 | Hofmann-Cerfontaine |

(Continued)

FOREIGN PATENT DOCUMENTS

| DE | 102008060513 | 6/2010 |
| EP | 0203683 | 12/1986 |

(Continued)

OTHER PUBLICATIONS

U.S. Appl. No. 60/594,300, Poidomani et al.
(Continued)

*Primary Examiner* — Allyson N Trail
(74) *Attorney, Agent, or Firm* — Andrew Veter

(57) ABSTRACT

A payment card (e.g., credit and/or debit card) is provided with a magnetic emulator operable to act as a magnetic stripe read-head detector and a data transmitter. A multiple layer flexible PCB may be fabricated to include multiple magnetic emulators. An emulator may include a coil that includes magnetic, ferromagnetic, or ferromagnetic, material in the coil's interior. Coils may be associated with zones. As a read-head is detected to move from zone-to-zone, coils may be activated to transmit information in those zones.

26 Claims, 17 Drawing Sheets

Related U.S. Application Data

No. 12/339,048, filed on Dec. 19, 2008, now Pat. No. 9,639,796.

(60) Provisional application No. 61/016,491, filed on Dec. 24, 2007, provisional application No. 61/026,846, filed on Feb. 7, 2008, provisional application No. 61/027,807, filed on Feb. 11, 2011, provisional application No. 61/081,003, filed on Jul. 15, 2008, provisional application No. 61/086,239, filed on Aug. 5, 2008, provisional application No. 61/090,423, filed on Aug. 20, 2008, provisional application No. 61/097,401, filed on Sep. 16, 2008, provisional application No. 61/112,766, filed on Nov. 9, 2008, provisional application No. 61/117,186, filed on Nov. 23, 2008, provisional application No. 61/119,366, filed on Dec. 2, 2008, provisional application No. 61/120,813, filed on Dec. 8, 2008.

(51) Int. Cl.

| | | |
|---|---|---|
| *G06K 19/077* | (2006.01) | |
| *G06Q 20/18* | (2012.01) | |
| *G06Q 20/20* | (2012.01) | |
| *G06Q 20/34* | (2012.01) | |
| *G06Q 20/38* | (2012.01) | |
| *G06Q 30/02* | (2012.01) | |
| *G06Q 30/06* | (2012.01) | |
| *G07F 7/08* | (2006.01) | |
| *G07F 7/10* | (2006.01) | |
| *G06K 19/06* | (2006.01) | |
| *G06K 7/08* | (2006.01) | |
| *G06K 19/073* | (2006.01) | |
| *G06K 7/00* | (2006.01) | |
| *G06F 3/0488* | (2013.01) | |
| *G06K 7/10* | (2006.01) | |
| *G06Q 20/40* | (2012.01) | |

(52) U.S. Cl.
CPC ..... *G06K 19/0704* (2013.01); *G06K 19/0723* (2013.01); *G06K 19/0725* (2013.01); *G06K 19/0775* (2013.01); *G06K 19/07345* (2013.01); *G06K 19/07703* (2013.01); *G06K 19/07705* (2013.01); *G06K 19/07707* (2013.01); *G06K 19/07709* (2013.01); *G06K 19/07749* (2013.01); *G06K 19/07766* (2013.01); *G06K 19/07769* (2013.01); *G06K 19/07773* (2013.01); *G06Q 20/18* (2013.01); *G06Q 20/20* (2013.01); *G06Q 20/34* (2013.01); *G06Q 20/341* (2013.01); *G06Q 20/3415* (2013.01); *G06Q 20/352* (2013.01); *G06Q 20/385* (2013.01); *G06Q 20/401* (2013.01); *G06Q 30/0222* (2013.01); *G06Q 30/0241* (2013.01); *G06Q 30/0277* (2013.01); *G06Q 30/0641* (2013.01); *G07F 7/0806* (2013.01); *G07F 7/1008* (2013.01)

(56) References Cited

U.S. PATENT DOCUMENTS

| | | |
|---|---|---|
| 4,614,861 A | 9/1986 | Pavlov et al. |
| 4,667,087 A | 5/1987 | Quintana |
| 4,701,601 A | 10/1987 | Francini et al. |
| 4,720,860 A | 1/1988 | Weiss |
| 4,786,791 A | 11/1988 | Hodama |
| 4,791,283 A | 12/1988 | Burkhardt |
| 4,797,542 A | 1/1989 | Hara |
| 5,038,251 A | 8/1991 | Sugiyama et al. |
| 5,168,520 A | 12/1992 | Weiss |
| 5,237,614 A | 8/1993 | Weiss |
| 5,276,311 A | 1/1994 | Hennige |
| 5,291,068 A | 3/1994 | Rammel |
| 5,347,580 A | 9/1994 | Molva et al. |
| 5,361,062 A | 11/1994 | Weiss et al. |
| 5,412,199 A | 5/1995 | Finkelstein et al. |
| 5,434,398 A | 7/1995 | Goldberg |
| 5,434,405 A | 7/1995 | Finkelstein et al. |
| 5,478,994 A | 12/1995 | Rahman |
| 5,479,512 A | 12/1995 | Weiss |
| 5,484,997 A | 1/1996 | Haynes |
| 5,485,519 A | 1/1996 | Weiss |
| 5,585,787 A | 12/1996 | Wallerstein |
| 5,591,949 A | 1/1997 | Bernstein |
| 5,608,203 A | 3/1997 | Finkelstein et al. |
| 5,623,552 A | 4/1997 | Lane |
| 5,657,388 A | 8/1997 | Weiss |
| 5,834,747 A | 11/1998 | Cooper |
| 5,834,756 A | 11/1998 | Gutman et al. |
| 5,856,661 A | 1/1999 | Finkelstein et al. |
| 5,864,623 A | 1/1999 | Messina et al. |
| 5,866,949 A | 2/1999 | Scheuller |
| 5,907,142 A | 5/1999 | Kelsey |
| 5,907,350 A | 5/1999 | Nemirofsky |
| 5,913,203 A | 6/1999 | Wong et al. |
| 5,937,394 A | 8/1999 | Wong et al. |
| 5,955,021 A | 9/1999 | Tiffany, III |
| 5,955,961 A | 9/1999 | Wallerstein |
| 5,956,699 A | 9/1999 | Wong et al. |
| 6,005,691 A | 12/1999 | Grot |
| 6,025,054 A | 2/2000 | Tiffany, III |
| 6,045,043 A | 4/2000 | Bashan et al. |
| 6,076,163 A | 6/2000 | Hoffstein et al. |
| 6,085,320 A | 7/2000 | Kaliski |
| 6,095,416 A | 8/2000 | Grant et al. |
| 6,129,274 A | 10/2000 | Suzuki |
| 6,130,621 A | 10/2000 | Weiss |
| 6,145,079 A | 11/2000 | Mitty et al. |
| 6,157,920 A | 12/2000 | Jakobsson et al. |
| 6,161,181 A | 12/2000 | Haynes, III et al. |
| 6,176,430 B1 | 1/2001 | Finkelstein et al. |
| 6,182,894 B1 | 2/2001 | Hackett et al. |
| 6,189,098 B1 | 2/2001 | Kaliski |
| 6,199,052 B1 | 3/2001 | Mitty et al. |
| 6,202,926 B1 | 3/2001 | Ito et al. |
| 6,206,293 B1 | 3/2001 | Gutman et al. |
| 6,240,184 B1 | 5/2001 | Huynh et al. |
| 6,241,153 B1 | 6/2001 | Tiffany, III |
| 6,256,873 B1 | 7/2001 | Tiffany, III |
| 6,269,163 B1 | 7/2001 | Rivest et al. |
| 6,286,022 B1 | 9/2001 | Kaliski et al. |
| 6,308,890 B1 | 10/2001 | Cooper |
| 6,313,724 B1 | 11/2001 | Osterweil |
| 6,422,462 B1 | 4/2002 | Cohen |
| 6,389,442 B1 | 5/2002 | Yin et al. |
| 6,393,447 B1 | 5/2002 | Jakobsson et al. |
| 6,411,715 B1 | 6/2002 | Liskov et al. |
| 6,446,052 B1 | 9/2002 | Juels |
| 6,460,141 B1 | 10/2002 | Olden |
| 6,507,913 B1* | 1/2003 | Shamir ............... G06K 19/073 |
| | | 713/300 |
| 6,592,044 B1 | 7/2003 | Wong et al. |
| 6,607,127 B2 | 8/2003 | Wong |
| 6,609,654 B1 | 8/2003 | Anderson et al. |
| 6,631,849 B2 | 10/2003 | Blossom |
| 6,655,585 B2 | 12/2003 | Shinn |
| 6,681,988 B2 | 1/2004 | Stack et al. |
| 6,705,520 B1 | 3/2004 | Pitroda et al. |
| 6,755,341 B1 | 6/2004 | Wong et al. |
| 6,764,005 B2 | 7/2004 | Cooper |
| 6,769,607 B1 | 8/2004 | Pitroda et al. |
| 6,769,618 B1 | 8/2004 | Finkelstein |
| 6,805,288 B2 | 10/2004 | Routhenstein et al. |
| 6,811,082 B2 | 11/2004 | Wong |
| 6,813,354 B1 | 11/2004 | Jakobsson et al. |
| 6,817,532 B2 | 11/2004 | Finkelstein |
| 6,873,974 B1 | 3/2005 | Schutzer |
| 6,902,116 B2 | 6/2005 | Finkelstein |

(56) References Cited

U.S. PATENT DOCUMENTS

| | | |
|---|---|---|
| 6,929,550 B2 | 8/2005 | Hisada |
| 6,970,070 B2 | 11/2005 | Juels et al. |
| 6,980,969 B1 | 12/2005 | Tuchler et al. |
| 6,985,583 B1 | 1/2006 | Brainard et al. |
| 6,991,155 B2 | 1/2006 | Burchette, Jr. |
| 7,013,030 B2 | 3/2006 | Wong et al. |
| 7,035,443 B2 | 4/2006 | Wong |
| 7,039,221 B1 | 5/2006 | Tumey et al. |
| 7,039,223 B2 | 5/2006 | Wong |
| 7,044,394 B2 | 5/2006 | Brown |
| 7,051,929 B2 | 5/2006 | Li |
| 7,083,094 B2 | 8/2006 | Cooper |
| 7,097,108 B2 | 8/2006 | Zellner et al. |
| 7,100,049 B2 | 8/2006 | Gasparini et al. |
| 7,100,821 B2 | 9/2006 | Rasti |
| 7,111,172 B1 | 9/2006 | Duane et al. |
| 7,114,652 B2 | 10/2006 | Moullette et al. |
| 7,136,514 B1 | 11/2006 | Wong |
| 7,140,550 B2 | 11/2006 | Ramachandran |
| 7,163,153 B2 | 1/2007 | Blossom |
| 7,195,154 B2 | 3/2007 | Routhenstein |
| 7,197,639 B1 | 3/2007 | Juels et al. |
| 7,219,368 B2 | 5/2007 | Juels et al. |
| 7,225,537 B2 | 6/2007 | Reed |
| 7,225,994 B2 | 6/2007 | Finkelstein |
| 7,246,752 B2 | 7/2007 | Brown |
| 7,298,243 B2 | 11/2007 | Juels et al. |
| 7,306,144 B2 | 12/2007 | Moore |
| 7,334,732 B2 | 2/2008 | Cooper |
| 7,337,326 B2 | 2/2008 | Palmer et al. |
| 7,346,775 B2 | 3/2008 | Gasparini et al. |
| 7,356,696 B1 | 4/2008 | Jakobsson et al. |
| 7,357,319 B1 | 4/2008 | Lin et al. |
| 7,359,507 B2 | 4/2008 | Kaliski |
| 7,360,688 B1 | 4/2008 | Harris |
| 7,363,494 B2 | 4/2008 | Brainard et al. |
| 7,380,710 B2 | 6/2008 | Brown |
| 7,398,253 B1 | 7/2008 | Pinnell |
| 7,404,087 B2 | 7/2008 | Teunen |
| 7,424,570 B2 | 9/2008 | D'Albore et al. |
| 7,427,033 B1 | 9/2008 | Roskind |
| 7,454,349 B2 | 11/2008 | Teunen et al. |
| 7,461,250 B1 | 12/2008 | Duane et al. |
| 7,461,399 B2 | 12/2008 | Juels et al. |
| 7,472,093 B2 | 12/2008 | Juels |
| 7,472,829 B2 | 1/2009 | Brown |
| 7,494,055 B2 | 2/2009 | Fernandes et al. |
| 7,502,467 B2 | 3/2009 | Brainard et al. |
| 7,502,933 B2 | 3/2009 | Jakobsson et al. |
| 7,503,485 B1 | 3/2009 | Routhenstein |
| 7,516,492 B1 | 4/2009 | Nisbet et al. |
| 7,516,883 B2 | 4/2009 | Hardesty |
| 7,523,301 B2 | 4/2009 | Nisbet et al. |
| 7,530,495 B2 | 5/2009 | Cooper |
| 7,532,104 B2 | 5/2009 | Juels |
| 7,543,739 B2 | 6/2009 | Brown et al. |
| 7,559,464 B2 | 7/2009 | Routhenstein |
| 7,562,221 B2 | 7/2009 | Nystrom et al. |
| 7,562,222 B2 | 7/2009 | Gasparini et al. |
| 7,580,898 B2 | 8/2009 | Brown et al. |
| 7,584,153 B2 | 9/2009 | Brown et al. |
| 7,591,426 B2 | 9/2009 | Osterweil et al. |
| 7,591,427 B2 | 9/2009 | Osterweil |
| 7,599,192 B2 | 10/2009 | Pennaz et al. |
| 7,602,904 B2 | 10/2009 | Juels et al. |
| 7,631,804 B2 | 12/2009 | Brown |
| 7,639,537 B2 | 12/2009 | Sepe et al. |
| 7,641,124 B2 | 1/2010 | Brown et al. |
| 7,660,902 B2 | 2/2010 | Graham et al. |
| 7,681,232 B2 | 3/2010 | Nordentoft et al. |
| 7,828,207 B2 | 11/2010 | Cooper |
| 2001/0034702 A1 | 10/2001 | Mockett et al. |
| 2001/0047335 A1 | 11/2001 | Arndt et al. |
| 2002/0043566 A1 | 4/2002 | Goodman et al. |
| 2002/0059114 A1 | 5/2002 | Cockrill et al. |
| 2002/0082989 A1 | 6/2002 | Fife et al. |
| 2002/0096570 A1 | 7/2002 | Wong et al. |
| 2002/0108066 A1 | 8/2002 | Masui |
| 2002/0120583 A1 | 8/2002 | Keresman, III et al. |
| 2003/0034388 A1 | 2/2003 | Routhenstein et al. |
| 2003/0042316 A1 | 3/2003 | Teraura |
| 2003/0052168 A1 | 3/2003 | Wong |
| 2003/0057278 A1 | 3/2003 | Wong |
| 2003/0116635 A1 | 6/2003 | Taban |
| 2003/0152253 A1 | 8/2003 | Wong |
| 2003/0163287 A1 | 8/2003 | Vock et al. |
| 2003/0173409 A1 | 9/2003 | Vogt et al. |
| 2003/0179909 A1 | 9/2003 | Wong et al. |
| 2003/0179910 A1 | 9/2003 | Wong |
| 2003/0226899 A1 | 12/2003 | Finkelstein |
| 2004/0035942 A1 | 2/2004 | Silverman |
| 2004/0052034 A1 | 3/2004 | Senba et al. |
| 2004/0097054 A1 | 5/2004 | Abe |
| 2004/0127256 A1 | 7/2004 | Goldthwaite |
| 2004/0133787 A1 | 7/2004 | Doughty |
| 2004/0162732 A1 | 8/2004 | Rahim et al. |
| 2004/0172535 A1 | 9/2004 | Jakobsson |
| 2004/0177045 A1 | 9/2004 | Brown |
| 2004/0179718 A1 | 9/2004 | Chou |
| 2005/0025117 A1* | 2/2005 | Inagaki .......... H04W 4/80 370/350 |
| 2005/0043997 A1 | 2/2005 | Sahata et al. |
| 2005/0080747 A1 | 4/2005 | Anderson et al. |
| 2005/0086160 A1 | 4/2005 | Wong et al. |
| 2005/0086177 A1 | 4/2005 | Anderson et al. |
| 2005/0116026 A1 | 6/2005 | Burger et al. |
| 2005/0119940 A1 | 6/2005 | Concilio et al. |
| 2005/0154643 A1 | 7/2005 | Doan et al. |
| 2005/0194452 A1 | 9/2005 | Nordentoft et al. |
| 2005/0228959 A1 | 10/2005 | D'Albore et al. |
| 2006/0000900 A1 | 1/2006 | Fernandes et al. |
| 2006/0037073 A1 | 2/2006 | Juels et al. |
| 2006/0041759 A1 | 2/2006 | Kaliski et al. |
| 2006/0085328 A1 | 4/2006 | Cohen et al. |
| 2006/0091223 A1 | 5/2006 | Zellner |
| 2006/0161435 A1 | 7/2006 | Atef et al. |
| 2006/0161789 A1 | 7/2006 | Doughty et al. |
| 2006/0163353 A1 | 7/2006 | Moulette et al. |
| 2006/0174104 A1 | 8/2006 | Crichton et al. |
| 2006/0196931 A1 | 9/2006 | Holtmanns et al. |
| 2006/0214866 A1 | 9/2006 | Araki et al. |
| 2006/0256961 A1 | 11/2006 | Brainard et al. |
| 2006/0283958 A1 | 12/2006 | Osterweil |
| 2006/0289632 A1 | 12/2006 | Walker |
| 2007/0034700 A1* | 2/2007 | Poidomani ......... G06K 19/0702 235/492 |
| 2007/0063025 A1 | 3/2007 | Blossom |
| 2007/0063776 A1 | 3/2007 | Okuda |
| 2007/0114274 A1 | 5/2007 | Gibbs et al. |
| 2007/0124321 A1 | 5/2007 | Szydlo |
| 2007/0131759 A1 | 6/2007 | Cox et al. |
| 2007/0152052 A1 | 7/2007 | Sines |
| 2007/0152070 A1 | 7/2007 | D'Albore |
| 2007/0152072 A1 | 7/2007 | Frallicciardi et al. |
| 2007/0153487 A1 | 7/2007 | Frallicciardi et al. |
| 2007/0174614 A1 | 7/2007 | Duane et al. |
| 2007/0192249 A1 | 8/2007 | Biffle et al. |
| 2007/0241183 A1 | 10/2007 | Brown et al. |
| 2007/0241201 A1 | 10/2007 | Brown et al. |
| 2007/0256123 A1 | 11/2007 | Duane et al. |
| 2007/0285246 A1 | 12/2007 | Koyoma |
| 2007/0291753 A1 | 12/2007 | Romano |
| 2008/0005510 A1 | 1/2008 | Sepe et al. |
| 2008/0008315 A1 | 1/2008 | Fontana et al. |
| 2008/0008322 A1 | 1/2008 | Fontana et al. |
| 2008/0010675 A1 | 1/2008 | Massascusa et al. |
| 2008/0016351 A1 | 1/2008 | Fontana et al. |
| 2008/0019507 A1 | 1/2008 | Fontana et al. |
| 2008/0028447 A1 | 1/2008 | O'Malley et al. |
| 2008/0040271 A1 | 2/2008 | Hammad et al. |
| 2008/0040276 A1 | 2/2008 | Hammad et al. |
| 2008/0058016 A1 | 3/2008 | Di Maggio et al. |
| 2008/0059379 A1 | 3/2008 | Ramaci et al. |
| 2008/0096326 A1 | 4/2008 | Reed |

(56) References Cited

U.S. PATENT DOCUMENTS

| | | |
|---|---|---|
| 2008/0110983 A1 | 5/2008 | Ashfield |
| 2008/0116285 A1 | 5/2008 | Shoemaker |
| 2008/0121726 A1 | 5/2008 | Brady et al. |
| 2008/0126398 A1 | 5/2008 | Cimino |
| 2008/0128515 A1 | 6/2008 | Di Iorio |
| 2008/0140536 A1 | 6/2008 | Ruiz |
| 2008/0148394 A1 | 6/2008 | Poidomani et al. |
| 2008/0201264 A1 | 8/2008 | Brown et al. |
| 2008/0209550 A1 | 8/2008 | Di Iorio |
| 2008/0262825 A1 | 10/2008 | Haid et al. |
| 2008/0288699 A1 | 11/2008 | Chichierchia |
| 2008/0294930 A1 | 11/2008 | Varone et al. |
| 2008/0302877 A1 | 12/2008 | Musella et al. |
| 2009/0013122 A1 | 1/2009 | Sepe et al. |
| 2009/0036147 A1 | 2/2009 | Romano |
| 2009/0037275 A1 | 2/2009 | Pollio |
| 2009/0046522 A1 | 2/2009 | Sepe et al. |
| 2009/0108064 A1 | 4/2009 | Fernandes et al. |
| 2009/0143104 A1 | 6/2009 | Loh |
| 2009/0150295 A1 | 6/2009 | Hatch et al. |
| 2009/0152365 A1 | 6/2009 | Li et al. |
| 2009/0159663 A1 | 6/2009 | Mullen |
| 2009/0159673 A1 | 6/2009 | Mullen |
| 2009/0159689 A1 | 6/2009 | Mullen |
| 2009/0170432 A1 | 7/2009 | Lortz |
| 2009/0191811 A1 | 7/2009 | Griffin |
| 2009/0210308 A1 | 8/2009 | Toomer |
| 2009/0222383 A1 | 9/2009 | Tato |
| 2009/0242648 A1 | 10/2009 | Di Sirio et al. |
| 2009/0244858 A1 | 10/2009 | Di Sirio et al. |
| 2009/0253460 A1 | 10/2009 | Varone et al. |
| 2009/0255996 A1 | 10/2009 | Brown et al. |
| 2009/0288012 A1 | 11/2009 | Hertel |
| 2009/0290704 A1 | 11/2009 | Cimino |
| 2009/0303885 A1 | 12/2009 | Longo |
| 2010/0019033 A1 | 1/2010 | Jolivet |
| 2010/0023449 A1 | 1/2010 | Skowronek |
| 2010/0045627 A1 | 2/2010 | Kennedy |
| 2010/0066701 A1 | 3/2010 | Ningrat |
| 2010/0078472 A1 | 4/2010 | Lin et al. |
| 2010/0108771 A1 | 5/2010 | Wong |
| 2010/0153269 A1 | 6/2010 | McCabe |
| 2010/0230793 A1 | 9/2010 | Kudose |
| 2010/0265037 A1 | 10/2010 | Domsten et al. |
| 2010/0270373 A1 | 10/2010 | Poidomani et al. |
| 2010/0304670 A1 | 12/2010 | Shuo |
| 2011/0028184 A1 | 2/2011 | Cooper |
| 2011/0066550 A1 | 3/2011 | Shank |

FOREIGN PATENT DOCUMENTS

| | | |
|---|---|---|
| GB | 2259815 | 3/1993 |
| GB | 2420098 | 5/2006 |
| JP | S63155188 | 6/1988 |
| JP | 05210770 | 8/1993 |
| JP | 05210770 A | 8/1993 |
| JP | H06150078 | 5/1994 |
| JP | 01194392 | 7/2001 |
| JP | 01194392 A | 7/2001 |
| JP | 2005010964 | 1/2005 |
| JP | 2005056540 A | 3/2005 |
| JP | 2005190363 | 7/2005 |
| JP | 2006195925 | 7/2006 |
| JP | 2006252160 | 9/2006 |
| JP | 2007172214 | 7/2007 |
| JP | 2008225626 | 9/2008 |
| JP | 2009037495 | 2/2009 |
| JP | 2010044730 | 2/2010 |
| JP | 2010086026 | 4/2010 |
| JP | 2011134298 | 7/2011 |
| KR | 200287641 Y1 | 8/2002 |
| WO | WO1989001672 | 2/1989 |
| WO | WO9852735 | 11/1998 |
| WO | WO0247019 | 6/2002 |
| WO | WO06066322 | 6/2006 |
| WO | WO2006078910 | 7/2006 |
| WO | WO06080929 | 8/2006 |
| WO | WO06105092 | 10/2006 |
| WO | WO06116772 | 11/2006 |
| WO | WO07141779 | 12/2007 |
| WO | WO08064403 | 6/2008 |
| WO | WO2008066806 | 6/2008 |

OTHER PUBLICATIONS

U.S. Appl. No. 60/675,388, Poidomani et al.
The Bank Credit Card Business. Second Edition, American Bankers Association, Washington, D.C., 1996.
A Day in the Life of a Flux Reversal. http://www.phrack/org/issues. html?issue=37&id=6#article. As viewed on Apr. 12, 2010.
Dynamic Virtual Credit Card Numbers. http://homes.cerias.purdue. edu/~jtli/paper/fc07.pdf. As viewed on Apr. 12, 2010.
USPTO, International Search Report, dated Apr. 28, 2009.
English translation of JP 05210770 A.
EPO, Extended European Search Report, dated Jan. 26, 2012.
U.S. Appl. No. 30/594,300, Poidomani et al.
English translation of JP 05210770.
Examination Report dated Nov. 9, 2016, received from Australian Patent Office for Australian Patent Application No. 2011218216.
Examination Report dated Sep. 19, 2017, received from Australian Patent Office for Australian Patent Application No. 2016259296.
Examination Report dated Feb. 17, 2016, received from Australian Patent Office for Australian Patent Application No. 2011255568.
Examination Report dated Feb. 13, 2017, received from Australian Patent Office for Australian Patent Application No. 2011255568.
Examination Report dated Oct. 30, 2017, received from Australian Patent Office for Australian Patent Application No. 2017201100.
Examination Report dated Feb. 23, 2016, received from Australian Patent Office for Australian Patent Application No. 2011283665.
Examination Report dated Feb. 23, 2017, received from Australian Patent Office for Australian Patent Application No. 2011283665.
Examination Report dated Aug. 25, 2016, received from Australian Patent Office for Australian Patent Application No. 2012240353.
Examination Report dated Feb. 17, 2016, received from Australian Patent Office for Australian Patent Application No. 2017219095.
Examination Report dated Jun. 14, 2016, received from Australian Patent Office for Australian Patent Application No. 2012235439.
Examination Report dated May 12, 2017, received from Australian Patent Office for Australian Patent Application No. 2012235439.
Examination Report dated Jun. 13, 2017, received from Australian Patent Office for Australian Patent Application No. 2012235439.
Examination Report dated Mar. 29, 2018, received from Australian Patent Office for Australian Patent Application No. 2017204011.
Examination Report dated Oct. 11, 2012, received from Australian Patent Office for Australian Patent Application No. 2008340226.
Examination Report dated Oct. 11, 2016, received from Australian Patent Office for Australian Patent Application No. 2008340226.
Examination Requisition dated Mar. 29, 2016, received from Canadian Patent Office for Canadian Patent Application No. 2,789,461.
Examination Requisition dated Mar. 8, 2017, received from Canadian Patent Office for Canadian Patent Application No. 2,798,984.
Examination Requisition dated Feb. 22, 2018, received from Canadian Patent Office for Canadian Patent Application No. 2,805,310.
Examination Requisition dated Dec. 10, 2018, received from Canadian Patent Office for Canadian Patent Application No. 2,831,459.
Examination Requisition dated Jan. 18, 2018, received from Canadian Patent Office for Canadian Patent Application No. 2,831,464.
Examination Requisition dated Dec. 13, 2018, received from Canadian Patent Office for Canadian Patent Application No. 2,831,464.
Office Action dated Dec. 6, 2018, received from Indian Patent Office for Indian Patent Application No. Dec. 6, 2018.
Office Action dated Dec. 12, 2017, received from South Korean Patent Office for Korean Patent Application No. 2013-7029089.
English translation of Office Action dated Dec. 12, 2017, received from South Korean Patent Office for Korean Patent Application No. 2013-7029089.
Office Action dated May 28, 2018, received from South Korean Patent Office for Korean Patent Application No. 2013-7029089.

(56) References Cited

OTHER PUBLICATIONS

English translation of Office Action dated May 28, 2018, received from South Korean Patent Office for Korean Patent Application No. 2013-7029089.
Office Action dated Sep. 13, 2018, received from South Korean Patent Office for Korean Patent Application No. 2013-7029089.
English translation of Office Action dated Sep. 13, 2018, received from South Korean Patent Office for Korean Patent Application No. 2013-7029089.
Office Action dated Nov. 14, 2018, received from Japanese Patent Office for Japanese Patent Application No. 2017195295.
English translation of Office Action dated Nov. 14, 2018, received from Japanese Patent Office for Japanese Patent Application No. 2017195295.
Office Action dated Jun. 27, 2018, received from Japanese Patent Office for Japanese Patent Application No. 2016210782.
English translation of Office Action dated Jun. 27, 2018, received from Japanese Patent Office for Japanese Patent Application No. 2016210782.
Office Action dated Oct. 30, 2017, received from Japanese Patent Office for Japanese Patent Application No. 2016210782.
English translation of Office Action dated Oct. 30, 2017, received from Japanese Patent Office for Japanese Patent Application No. 2016210782.
Office Action dated Aug. 29, 2018, received from Japanese Patent Office for Japanese Patent Application No. 2016153360.
English translation of Office Action dated Aug. 29, 2018, received from Japanese Patent Office for Japanese Patent Application No. 2016153360.
Office Action dated Oct. 12, 2017, received from Japanese Patent Office for Japanese Patent Application No. 2016153360.
English translation of Office Action dated Oct. 12, 2017, received from Japanese Patent Office for Japanese Patent Application No. 2016153360.
Office Action dated Jun. 5, 2016, received from Japanese Patent Office for Japanese Patent Application No. 2016000177.
English translation of Office Action dated Jun. 5, 2016, received from Japanese Patent Office for Japanese Patent Application No. 2016000177.
Office Action dated Nov. 9, 2016, received from Japanese Patent Office for Japanese Patent Application No. 2016000177.
English translation of Office Action dated Nov. 9, 2016, received from Japanese Patent Office for Japanese Patent Application No. 2016000177.
Office Action dated Jun. 27, 2016, received from Japanese Patent Office for Japanese Patent Application No. 2013522010.
English translation of Office Action dated Jun. 27, 2016, received from Japanese Patent Office for Japanese Patent Application No. 2013522010.
Office Action dated Jul. 29, 2017, received from Japanese Patent Office for Japanese Patent Application No. 2013522010.
English translation of Office Action dated Jul. 29, 2017, received from Japanese Patent Office for Japanese Patent Application No. 2013522010.
Office Action dated Apr. 4, 2016, received from Japanese Patent Office for Japanese Patent Application No. 2013533532.
English translation of Office Action dated Apr. 4, 2016, received from Japanese Patent Office for Japanese Patent Application No. 2013533532.
Office Action dated Mar. 18, 2015, received from Japanese Patent Office for Japanese Patent Application No. 2013533532.
English translation of Office Action dated Mar. 18, 2015, received from Japanese Patent Office for Japanese Patent Application No. 2013533532.
Office Action dated Dec. 2, 2015, received from Japanese Patent Office for Japanese Patent Application No. 2012553989.
English translation of Office Action dated Dec. 2, 2015, received from Japanese Patent Office for Japanese Patent Application No. 2012553989.
Office Action dated Nov. 4, 2014, received from Japanese Patent Office for Japanese Patent Application No. 2012553989.
English translation of Office Action dated Nov. 4, 2014, received from Japanese Patent Office for Japanese Patent Application No. 2012553989.
Summons to attend oral proceedings dated Sep. 18, 2013, received from European Patent Office for European Patent Application No. 08865573.3.
European Search Report dated Jan. 25, 2012, received from European Patent Office for European Patent Application No. 08865573.3.
European Search Report dated May 2, 2013, received from European Patent Office for European Patent Application No. 08865573.3.
Decision on Appeal dated May 5, 2014, received from European Patent Office for European Patent Application No. 08865573.3.
European Search Report dated Sep. 23, 2015, received from European Patent Office for European Patent Application No. 13752216.5.
Summons to attend oral proceedings dated Jul. 4, 2018, received from European Patent Office for European Patent Application No. 12783038.8.
European Search Report dated Feb. 27, 2015, received from European Patent Office for European Patent Application No. 12783038.8.
European Search Report dated Apr. 8, 2016, received from European Patent Office for European Patent Application No. 12783038.8.
European Search Report dated Oct. 19, 2017, received from European Patent Office for European Patent Application No. 17173592.1.
Summons to attend oral proceedings dated Sep. 19, 2016, received from European Patent Office for European Patent Application No. 12767357.2.
European Search Report dated Aug. 22, 2014, received from European Patent Office for European Patent Application No. 12767357.2.
European Search Report dated Aug. 18, 2015, received from European Patent Office for European Patent Application No. 12767357.2.
Decision on Appeal dated Mar. 30, 2017, received from European Patent Office for European Patent Application No. 12767357.2.
European Search Report dated Feb. 12, 2018, received from European Patent Office for European Patent Application No. 17182452.7.
Summons to attend oral proceedings dated Oct. 19, 2016, received from European Patent Office for European Patent Application No. 11813282.8.
European Search Report dated Jul. 22, 2014, received from European Patent Office for European Patent Application No. 11813282.8.
European Search Report dated Aug. 24, 2015, received from European Patent Office for European Patent Application No. 11813282.8.
Decision on Appeal dated Oct. 5, 2017, received from European Patent Office for European Patent Application No. 11813282.8.
European Search Report dated Oct. 7, 2016, received from European Patent Office for European Patent Application No. 16172188.1.
European Search Report dated Jun. 15, 2015, received from European Patent Office for European Patent Application No. 11784196.5.
European Search Report dated Nov. 10, 2015, received from European Patent Office for European Patent Application No. 11784196.5.
European Search Report dated Aug. 15, 2018, received from European Patent Office for European Patent Application No. 11784196.5.
European Search Report dated Dec. 18, 2017, received from European Patent Office for European Patent Application No. 11784196.5.

(56) References Cited

OTHER PUBLICATIONS

European Search Report dated Feb. 7, 2014, received from European Patent Office for European Patent Application No. 11745157.5.
European Search Report dated Oct. 29, 2018, received from European Patent Office for European Patent Application No. 11745157.5.
European Search Report dated Jun. 20, 2017, received from European Patent Office for European Patent Application No. 11745157.5.
European Search Report dated Jul. 7, 2016, received from European Patent Office for European Patent Application No. 11745157.5.
Patent Examination Report No. 1, Australian Patent Application No. 2008340226, dated Oct. 11, 2012.
Article 94(3) EPC communication in European Patent Application No. 08865573.3-2221, dated Feb. 5, 2013.
Magnetic stripe card, Mindmatrix (this document is presented by the European Patent Office without a link).
Summons to Oral Proceedings in European Patent Application No. 08865573.3-2221, dated Sep. 18, 2013.
Digital Transactions Trends in the Electronic Exchange of Value. Samsung Pay's Mag-Stripe Emulation Advantage might be Short Lived.
Translation of KR200287641Y1.
Translation of JP2005056540A.

\* cited by examiner

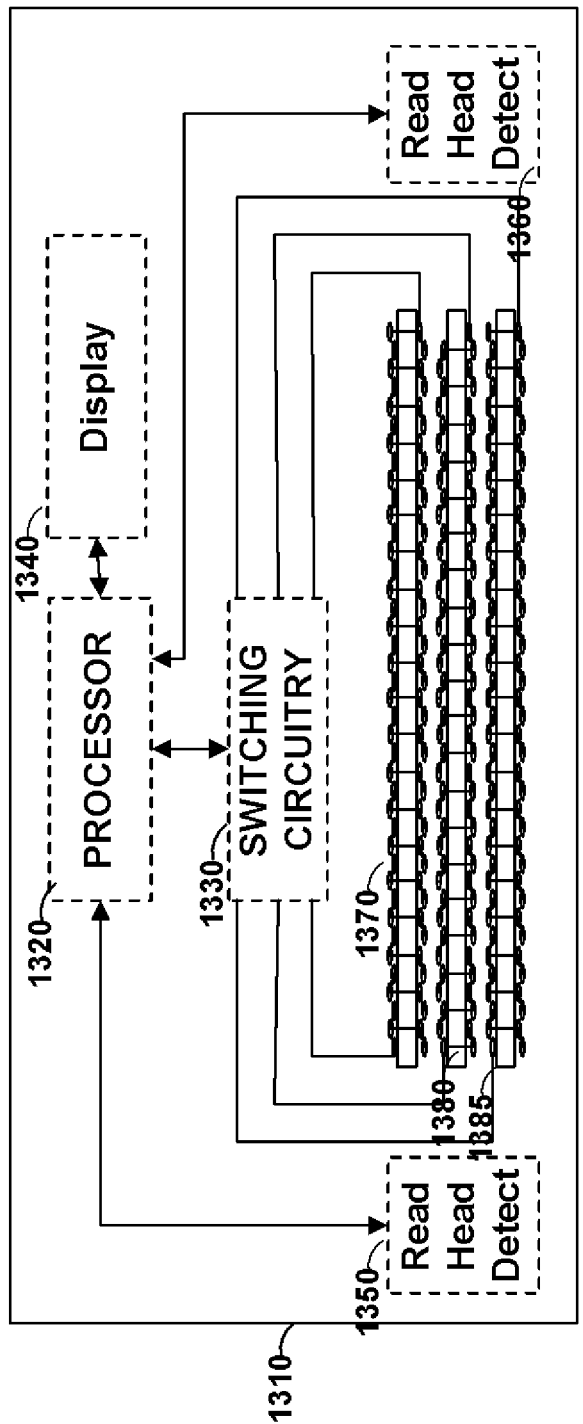
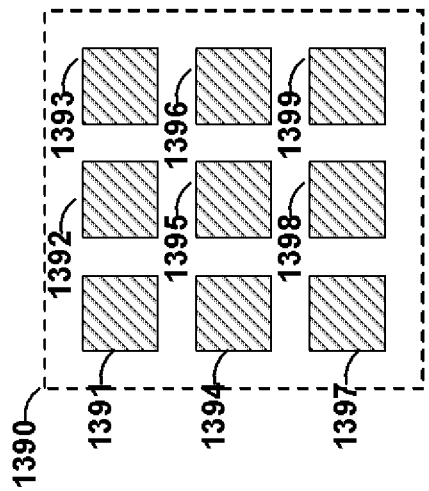
FIG. 13

CARDS AND DEVICES WITH MAGNETIC EMULATORS WITH ZONING CONTROL AND ADVANCED INTERIORS

CROSS-REFERENCE TO RELATED APPLICATIONS

This application is a continuation of U.S. patent application Ser. No. 15/583,356, entitled "CARDS AND DEVICES WITH MAGNETIC EMULATORS WITH ZONING CONTROL AND ADVANCED INTERIORS" filed on May 1, 2017, which is a continuation of U.S. patent application Ser. No. 12/339,048, entitled "CARDS AND DEVICES WITH MAGNETIC EMULATORS WITH ZONING CONTROL AND ADVANCED INTERIORS" filed on Dec. 19, 2008, which claims the benefit of U.S. Provisional Patent Application Nos. 61/016,491 filed on Dec. 24, 2007, 61/026,846 filed on Feb. 7, 2008, 61/027,807 filed on Feb. 11, 2008, 61/081,003 filed on Jul. 15, 2008, 61/086,239 filed on Aug. 5, 2008, 61/090,423 filed on Aug. 20, 2008, 61/097,401 filed Sep. 16, 2008, 61/112,766 filed on Nov. 9, 2008, 61/117,186 filed on Nov. 23, 2008, 61/119,366 filed on Dec. 2, 2008, and 61/120,813 filed on Dec. 8, 2008, all of which are hereby incorporated by reference herein in their entirety.

BACKGROUND OF THE INVENTION

This invention relates to magnetic cards and payment systems.

SUMMARY OF THE INVENTION

A card is provided, such as a credit card or security card, that may transmit information to a magnetic stripe reader via a magnetic emulator. The magnetic emulator may be, for example, a circuit that emits electromagnetic fields operable to electrically couple with a read-head of a magnetic stripe reader such that data may be transmitted from the circuit to the magnetic stripe reader. The emulator may be operated serially such that information is transmitted serially to a magnetic stripe reader. Alternatively, for example, portions of a magnetic emulator may emit different electromagnetic fields at a particular instance such that the emulator is operated to provide physically parallel, instantaneous data. Alternatively still, a magnetic medium may be provided and a circuit may be provided to change the magnetic properties of the magnetic medium such that a magnetic stripe reader is operable to read information written on the magnetic medium.

A processor may be provided on a card, or other device, that controls a magnetic emulator. The processor may be configured to operate the emulator such that the emulator transmits serial or parallel information. Particularly, the processor may decouple portions of an emulator from one another such that different portions of the emulator may transmit different information (e.g., transmit data in a parallel operation). The processor may couple portions of an emulator together (or drive the portions together) such that all portions of the emulator transmits the same information (e.g., transmit data in a serial operation). Alternatively, the processor may drive a portion of the emulator to transmit data using one method (e.g., serially) while the processor drives another portion of the emulator using a different method (e.g., in parallel).

The processor may drive an emulator through a switching circuit. The switching circuit may control the direction and magnitude of current that flows through at least a portion of an emulator such that the switching circuit controls the direction and magnitude of the electromagnetic field created by at least that portion of the emulator. An electromagnetic field may be generated by the emulator such that the emulator is operable to electrically couple with a read-head from a magnetic stripe reader without making physical contact with the read-head. Particularly, for example, an emulator that is driven with increased current can be operable to couple with the read-head of a magnetic stripe reader even when placed outside and within the proximity of (e.g., 0.25 inches or more) the read-head.

A processor may detect, for example, the presence of a read-head of a magnetic stripe reader by receiving signals from a magnetic stripe reader detector and, in response, the processor may drive a magnetic emulator in a manner that allows the emulator to couple with the magnetic stripe reader. More than one emulator may be provided on a card or other device and a processor may drive such emulators in a variety of different manners.

A circuit may be provided on a credit card that is operable to receive data from a device, such as a magnetic stripe. In this manner, a card, or other device, may communicate bi-directionally with a device.

An emulator may communicate with a magnetic stripe reader outside of, for example, the housing of a magnetic stripe reader. Accordingly, for example, the emulator may be provided in devices other than cards sized to fit inside of the reading area of a magnetic stripe reader. In other words, for example, the emulator may be located in a device that is thicker than a card—yet the emulator can still communicate with one or more read-heads located in a magnetic stripe reader. Such a device may be, for example, a security token, a wireless communications device, a laptop, a Personal Digital Assistant (PDA), a physical lock key to a house and/or car, or any other device.

Dynamic information may be provided by a processor located on the card, or other device, and communicated through a magnetic emulator. Such dynamic information may, for example, change based on time. For example, the dynamic information may be periodically encrypted differently. One or more displays may be located on a card, or other device, such that the dynamic information may be displayed to a user through the display. Buttons may be provided to accept input from a user to, for example, control the operation of the card or other device.

Dynamic information may include, for example, a dynamic number that is used as, or part of, a number for a credit card number, debit card number, payment card number, and/or payment verification code. Dynamic information may also include, for example, a student identification number or medical identification number. Dynamic information may also, for example, include alphanumeric information such that a dynamic account name is provided.

Magnetic emulation circuits may be provided that generate electromagnetic fields. The emulation circuits may have active regions operable to be read by a read-head of a magnetic stripe reader. The emulation circuits may also have, for example, non-active regions that are not operable to be read by a read-head of a magnetic stripe reader. Multiple emulation circuits may be provided on different layers such that the active regions of multiple emulation circuits provide a read-head of a magnetic stripe reader continuous visibility to active regions while a card is swiped. A coil may include return paths that may be able to, for example, transmit information to a read-head but may communicate information using electromagnetic fields in an opposite direction than the primary paths (e.g., active regions) of a coil such that a reader may not be able discern a set of when the reader picks up part of the information from a return path followed by part of the information from a primary path (or vice versa).

Magnetic emulation circuits may extend across multiple tracks. However, the areas of such magnetic emulation circuits that extended to undesired tracks may be configured to be invisible to the read-heads for those tracks. For example, a magnetic emulator may produce magnetic fields that are not oriented properly to be picked up by unintended read-head(s) but that are oriented properly to be picked up by intended read-head(s).

Read-head detectors may be provided to determine, for example, when a card is being swiped and/or when a read-head is located over a particular portion of a card (e.g., a magnetic emulation circuit). A magnetic emulation circuit may be provided as, for example, a coil. Portions of such a coil may be utilized to detect a read-head while in other portions of the coil may be utilized to communicate information electromagnetically to a read-head. Accordingly, a coil may be utilized to detect a read-head and, after a read-head is detected, the coil may be utilized to, for example, serially transmit information to a magnetic stripe reader.

A read-head detector, or an array of read-head detectors, may be able to, for example, determine the type of reader that the card entered into. For example, a read-head detector array may determine, for example, when a motorized reader was utilized, an insertion reader was utilized, or a user-swipe reader was utilized. Such information may be stored and communicated to a remote storage device (e.g., a remote database). This stored information may be utilized to combat, for example, card cloning. For example, if a particular number of cards (e.g., 10 more) that made consecutive purchases from a machine (e.g., an ATM) detected more than one reader, then, for example, the system may make an autonomous determination that an illegal cloning device was located on front of that ATM machine. If, for example, multiple cards use a restaurant point-of-sale terminal and determine that multiple readers were used then, for example, a computer can make an autonomous determination that cloning may have occurred at the restaurant.

Cards may be swiped through the same reader multiple times for a number of reasons (e.g., mis-swipes). However, over a number of cards (e.g., 100), instances of cloning may become apparent. Additionally, for example, information about swipes that happened outside of a transaction (e.g., the period from which the card is active after an appropriate unlocking code is entered) may be transmitted to detect instances where a magnetic emulator was turned ON and read by a reader, but no transaction was received by a processing/authorization facility. Such information may be utilized to, for example, provide an alert that the user may have encountered, and tried to use, a fake ATM machine.

Multiple magnetic emulators may be coupled in series. Multiple magnetic emulators, or arrays of magnetic emulators, may be controlled independently. Emulators may be assigned zones and may be utilized to communicate information on a zone-by-zone basis. In doing so, for example, emulators that include coils with return paths may place those return paths in other zones. Accordingly, the primary paths for an emulator may be included in a zone to communicate information when that zone is activated. When other zones are activates, the return paths of the emulator may not interfere with the primary paths of other emulators that are attempting to communicate information. Read-head detectors may be utilized, for example, to provide information to a processor so that the processor may make a determination as to what zone, or zones, should be activated to communicate information at any given time.

Magnetic emulators, such as magnetic emulators that include coils, may be fabricated on multiple layers of either flexible or rigid printed circuit board. Accordingly, a coil may be fabricated over multiple layers. Materials may be placed in the interior of these coils to assist the coil in communicating information to a read-head. For example, two PCB layers may be utilized. The top layer may be utilized for one set of paths (e.g., primary paths) and the bottom layer may be utilize for another set of paths (e.g., return paths).

A material may be sandwiched between the two layers to assist in reducing the effect of the electromagnetic fields from one set of coil segments on the side of the material opposite that set of coil segments. Such an interior material may be insulated such that the material does not short the coil segments. Additionally, such an interior material may be chosen, for example, such that the material does not saturate when the coil is conducting current. The coil and material may run, for example, along the location of a track of magnetic data for a payment card.

A material may be placed and/or printed on a PCB layer and sandwiched between two other PCB layers. These two other layers may each include coil segments and vias. The middle layer may also include vias such that the material is fabricated to be located in the center of the coil. The material may take a cylindrical, rectangular, square, or any type of shape. Four layers may also be utilized, where the coil segments are printed on a surface of the exterior layers and one or more materials are printed and/or placed on/between the interior layers. A material may be a magnetic material, ferromagnetic material, ferrimagnetic material, or any type of material. For example, copper may be printed on a PCB layer and plated with a material (e.g., nickel, iron, chrome, tin, gold, platinum, cobalt, zinc, alloys). A material, for example, may have a relative permeability multiple times greater than the permeability of a vacuum. A material, for example, may have a permeability of 2 to 25,000 N/A^2. A material may include, for example, a permalloy, iron, steel, ferrite, nickel or any other material. A material may be an alloy such as a nickel-iron alloy. Such a nickel-iron alloy may include, for example, nickel (e.g., 75-85%), iron, copper, molybdenum and may be placed through one or more annealing processes. Annealing may occur before and/or after the material is placed/printed on a layer of material (e.g., a PCB layer or other layer). A similar and/or different material may be placed either above and/or below a portion, or the entire, set of paths on a layer for a coil. Accordingly, for example, a material may be placed in the interior of a coil as well as along a side of the coil.

BRIEF DESCRIPTION OF THE DRAWINGS

The principles and advantages of the present invention can be more clearly understood from the following detailed description considered in conjunction with the following drawings, in which the same reference numerals denote the same structural elements throughout, and in which:

FIG. 13 is an illustration of a card constructed in accordance with the principles of the present invention.

DETAILED DESCRIPTION OF THE INVENTION

Figure 1:
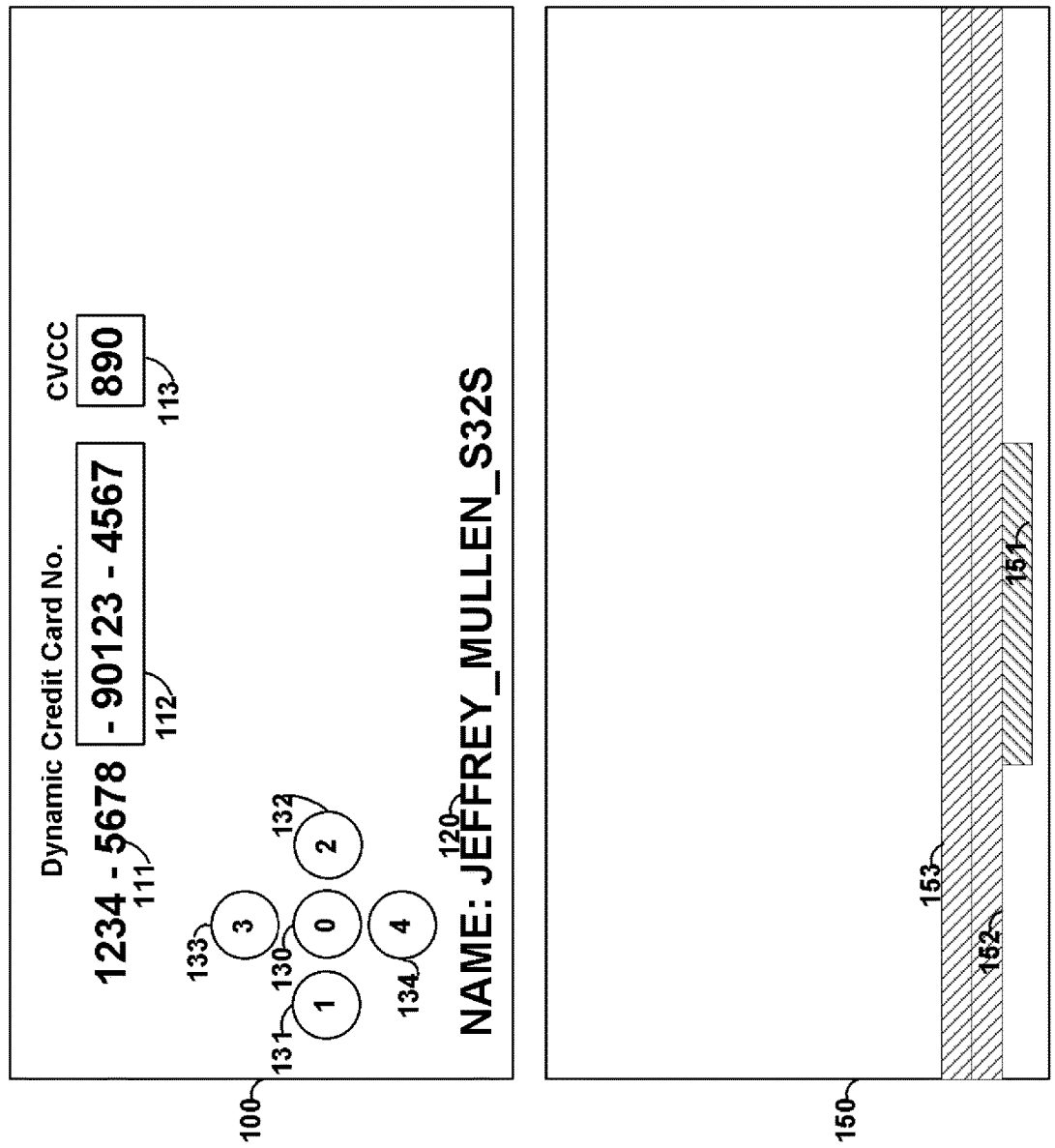
FIG. 1 is an illustration of cards constructed in accordance with the principles of the present invention.

FIG. 1 shows card 100 that includes printed information 111 and 120, displays 112 and 113, and buttons 130-134. Card 100 may be, for example, a payment card such as a credit card, debit card, and/or gift card or any other type of card (e.g., security access or identification card). Payment information, such as a credit/debit card number may be provided as static information 111, dynamic information 112 and/or 113, or any combination thereof.

For example, a particular number of digits of a credit card number (e.g., the last 3 digits) may be provided as dynamic information. Such dynamic information may be changed periodically (e.g., once every hour). Information may be changed via, for example, encryption. Software may be provided at, for example, the payment verification server that verifies the dynamic information for each period of time such that a payment can be validated and processed for a particular user. A user may be identified using, for example, static information that is used to form a credit card number or other static information (e.g., information 120). Additionally, identification information may be derived (e.g., embedded) in dynamic information. Persons skilled in the art will appreciate that a credit card number may have, for example, a length of 15 or 16 digits. A credit card number may also have a length of up to 19 digits. A verification code may be used with some payment systems and such a verification code may be provided statically on the card or may be provided as dynamic information. Such a verification code may be provided on a second display located on, for example, the front or rear surface of card 100. Alternatively, a verification code may be displayed on the same display as other dynamic information (e.g., dynamic information 112). A display may be, for example, a flexible electronic ink display. Such a flexible electronic ink display may, for example, utilize power to change displayed information, but may not utilize power to display information after the information is changed.

Card 150 may be provided. Card 150 may include static magnetic stripe tracks 153 and 152. Magnetic emulator 151 may be included and may be operable to electrically couple with a read-head of a magnetic stripe reader. Persons skilled in the art will appreciate that a read-head housing of a magnetic stripe reader may be provided with one, two, or three active read-heads that are operable to each couple with a separate magnetic track of information. A reader may also have more than one read-head housing and each read-head housing may be provided with one, two, or three active read-heads that are operable to each couple with a separate magnetic track of information. Such read-head housings may be provided different surfaces of a magnetic stripe reader. For example, the read-head housings may be provided on opposite walls of a trough sized to accept payment cards. Accordingly, the devices on the opposite sides of the trough may be able to read a credit card regardless of the direction that the credit card was swiped.

A magnetic emulator may be provided and may be positioned on card 150 such that when card 150 is swiped through a credit card reader, the magnetic emulator passes underneath, or in the proximity of, a read-head for a particular magnetic track. An emulator may be large enough to simultaneously pass beneath, or in the proximity of, multiple read-heads. Information may be transmitted, for example, serially to one or more read-heads. Information from different tracks of data may also be transmitted serially and the magnetic stripe reader may determine the different data received by utilize the starting and/or ending sentinels that define the information for each track. A magnetic emulator may also transmit a string of leading and/or ending zeros such that a magnetic reader may utilize such a string of zeros to provide self-clocking. In doing so, for example, information may be transmitted serially at high speeds to a magnetic stripe reader. For example, credit card information may be transmitted to a magnetic stripe reader at speeds up to, and greater than, 30 kHz).

Different emulators may be provided, and positioned, on card 150 to each couple with a different read-head and each emulator may provide different track information to those different read-heads. Read-head detectors may be utilized to detect when a read-head is over an emulator such that an emulator is controlled by a processor to operate when a read-head detector detects the appropriate presence of a read-head. In doing so, power may be saved. Additionally, the read-head detector may detect how many read-heads are reading the card and, accordingly, only communicate with the associated emulators. In doing so, additional power may be conserved. Accordingly, an emulator may be utilized to communicate dynamic information to a magnetic stripe reader. Such dynamic information may include, for example, dynamic payment card information that changes based on time.

A static magnetic stripe may be provided to transmit data for one or more tracks to a magnetic strip reader where dynamic information is not desired. Card 150, for example, may include static magnetic track 153 and static magnetic track 152. Information on static magnetic tracks 152 and 153 may be encoded via a magnetic stripe encoder. Emulator 151 may be included such that dynamic information may be communicated to a magnetic stripe reader, for example, without a magnetic stripe via an electromagnetic signal transmitted directly from emulator 151 to a read-head of a magnetic stripe reader. Any combination of emulators and static magnetic tracks may be utilized for a card or device (e.g., two magnetic emulators without any magnetic stripes).

One or more batteries, such as flexible lithium polymer batteries, may be utilized to form card 100. Such batteries may be electrically coupled in a serial combination to provide a source of power to the various components of card 100. Alternatively, separate batteries may provide power to different components of card 100. For example, a battery may provide power to a processor and/or display of card 100, while another battery provides a source of energy to one or more magnetic emulators of card 100. In doing so, for example, a processor may operate even after the battery that supplies power to an emulator completely discharges. Accordingly, the processor may provide information to another component of card 100. For example, the processor may display information on a display to indicate to a user that the magnetic emulator is not longer operational due to power exhaustion. Batteries may be, for example, rechargeable and contacts, or other devices, may be provided on card 100 such that the battery may be recharged.

Buttons (e.g., buttons 130-134) may be provided on a card. Such buttons may allow a user to manually provide information to a card. For example, a user may be provided with a personal identification code (e.g., a PIN) and such a personal identification code may be required to be manually inputted into a card using the buttons in order for the card to operate in a particular manner. For example, the use of a magnetic emulator or the use of a display may require a personal identification code.

By dynamically changing a portion of a user's credit card number, for example, credit card fraud is minimized. By allowing the dynamic information to displayed visually to a user, and changed magnetically on a card, user behavior change is minimized (with respect to a credit card with completely static information). By requiring the use of a personal identification code, the fraud associated with lost or stolen credit cards is minimized. Fraud associated with theft/loss is minimized as third party users do not know the personal identification code needed to operate particular aspects of a credit card with dynamic information.

Figure 2:
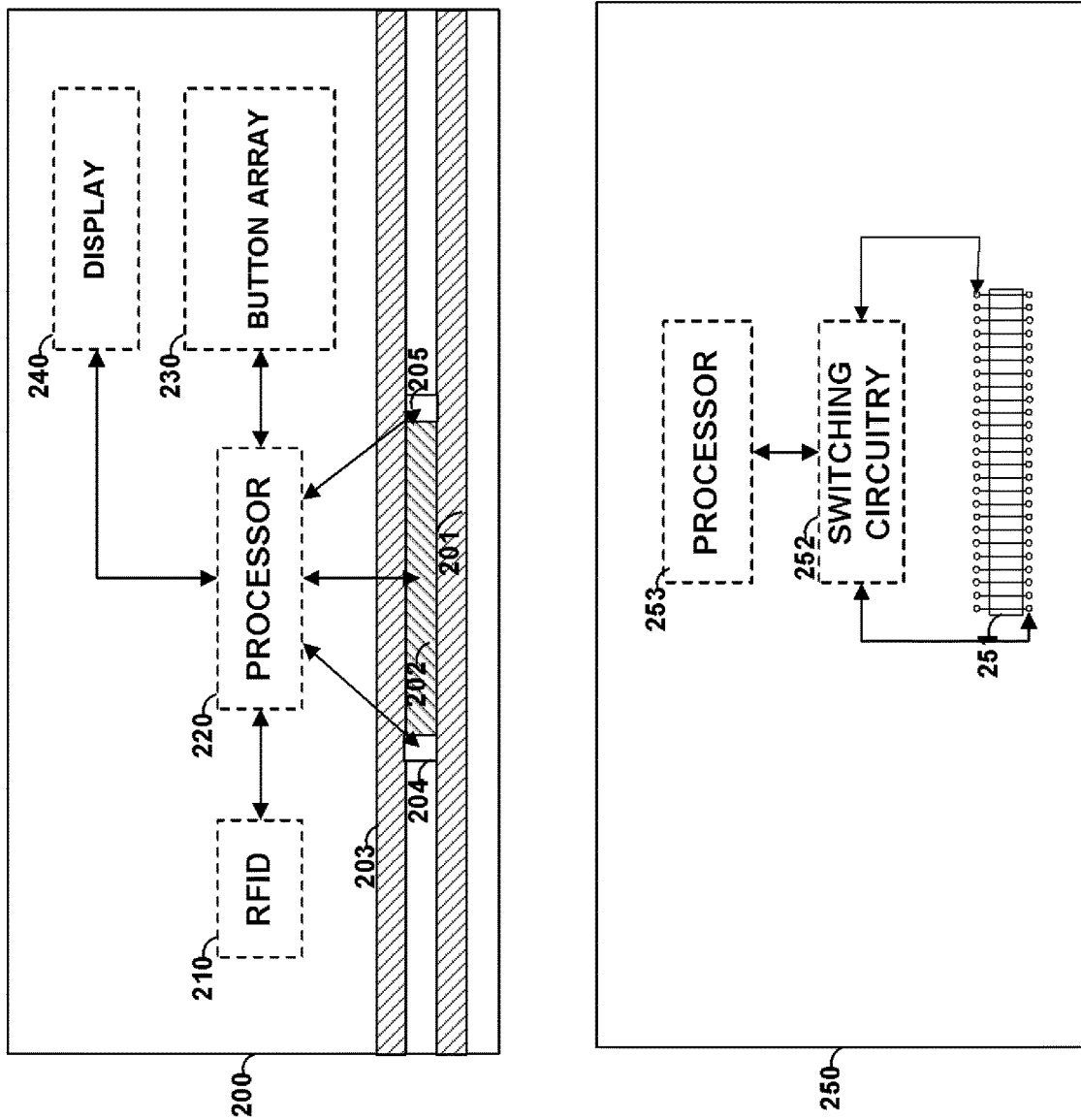
FIG. 2 is an illustration of cards constructed in accordance with the principles of the present invention.

FIG. 2 shows card 200. Card 200 may include, for example, static magnetic stripe track 203, static magnetic stripe track 201, and magnetic emulator 202 sandwiched between read-head detectors 204 and 205. A read-head detector may, for example, be provided as a circuit that detects, for example, changes in capacitance or mechanical coupling to a conductive material. Processor 220 may be provided to, for example, receive information from read-head detectors 204 and 205 and control emulator 202. Persons skilled in the art will appreciate that processor 220 may cause a current to flow through a coil of emulator 202 in a different direction to produce different electromagnetic fields. The transitions between the different electromagnetic fields may be sensed by a magnetic stripe reader as information. Accordingly, a magnetic emulator may transmit data serially while a read-head is electrically coupled with a magnetic reader.

RFID antenna 210 may be provided on card 200. Such an RFID antenna may be operable to transmit information provided by processor 220. In doing so, for example, processor 220 may communicate with an RFID device using RFID antenna 210 and may communicate with a magnetic stripe reader using magnetic emulator 202. Both RFID antenna 210 and magnetic emulator 202 may be utilized to communicate payment card information (e.g., credit card information) to a reader. Processor 240 may also be coupled to display 240 such that dynamic information can be displayed on display 240. Button array 230 may also be coupled to processor 220 such that the operation of card 200 may be controlled, at least in part, by manual input received by button array 230. A smart-card chip may, for example, be included on card 200 in lieu of, or in addition to, RFID 210.

Persons skilled in the art will appreciate that a static magnetic track may be a read-write track such that information may be written to a magnetic track from a magnetic stripe reader that includes a head operable to magnetically encode data onto a magnetic track. Information may be written to a magnetic track as part of a payment process (e.g., a credit card or debit card transaction). Persons skilled in the art will appreciate that a static magnetic track may include a magnetic material that includes ferromagnetic materials that provide for flux-reversals such that a magnetic stripe reader can read the flux-reversals from the static magnetic track. Persons skilled in the art will also appreciate that a magnetic emulator may communicate information that remains the same from payment card transaction to payment card transaction (e.g., static information) as well as information that changes between transactions (e.g., dynamic information).

A card may include magnetic emulators without, for example, including a static magnetic track. Read-head detectors may also be provided. Persons skilled in the art will appreciate that a magnetic reader may include the ability to read two tracks of information (e.g., may include at least two read-heads). All of the information needed to perform a financial transaction (e.g., a credit/debit card transaction) may be included on two magnetic tracks. Alternatively, all of the information needed to perform a financial transaction (e.g., a gift card transaction) may be included on one magnetic track. Accordingly, particular cards, or other devices, may include the ability, for example, to only transmit data associated with the tracks that are needed to complete a particular financial transaction. Persons skilled in the art will appreciate that for systems with three tracks of information, the bottom two tracks may be utilized for credit card information. Persons skilled in the art will also appreciate that a secure credit card transaction may be provided by only changing, for example, one of two magnetic tracks utilized in a credit card transaction (for those transactions that utilize two tracks). Accordingly, one track may be a static magnetic track constructed from a magnetic material and the other track may be provided as a magnetic emulator. Persons skilled in the art will also appreciate that numerous additional fields of data may be provided on a magnetic track in addition to a credit card number (or a security code). Dynamic information may be provided in such additional fields in order to complete a particular financial transaction. For example, such additional dynamic information may be numbers (or characters), encrypted with time and synced to software, at a validating server, operable to validate the encrypted number for a particular period of time.

Card 250 includes emulator 251 that includes a coil operable to communicate data serially to a magnetic stripe reader. Similarly, for example, emulator 251 may receive information for a magnetic stripe encoder. Persons skilled in the art will appreciate that a coil may run across the length of a card such that a read-head moves along the length of the coil and can receive information transmitted serially from the coil. The coil may extend into multiple tracks such that multiple read-heads receive information from the coil. Track information can be sent serially (e.g., track 1 information followed by track 2 information). Multiple coils may be driven separately and placed in different zones such that a single read-head moves from coil-to-coil (e.g., zone-tozone) and power is conserves as only coils in a particular zone (or zones) may be utilized to communicate information any particular time. Separate coils may be utilized for separate tracks. Materials may be placed in the interior of each coil to assist with manipulating the electromagnetic field produced by the coils. Material may be placed above or below a coil to further manipulate the electromagnetic field produced by the coil. Switching circuitry 252 may include, for example, one or more transistors that may be utilized to control the direction of current via emulator 251 (e.g., the polarity of voltage(s) across a drive resistor). For example, a coil may be utilized to transmit a string of information to a particular read-head. Different coils may transmit information at different speeds (or at the same speed). Different coils may transmit different amounts of information. For example, three coils may be provided. The coil closest to the bottom of the long-end of a card may transmit at least 79 characters. The coil next closest to the bottom of the long-end of a card may transmit at least 40 characters of information. The coil next closest to the bottom of the long-end of the card may transmit at least 107 characters. One or more coils may have different character sets (e.g., a 6-bit character set or a 7-bit character set). The last bit in a character may include, for example, a parity bit. Additional synching information may be transmitted before and after the data information to assist with synching a magnetic stripe reader. For example, a string of zeros may be communicated before and after communicating primary data. Characters may be included in the data information for other purposes such as an LRC character.

Figure 3:
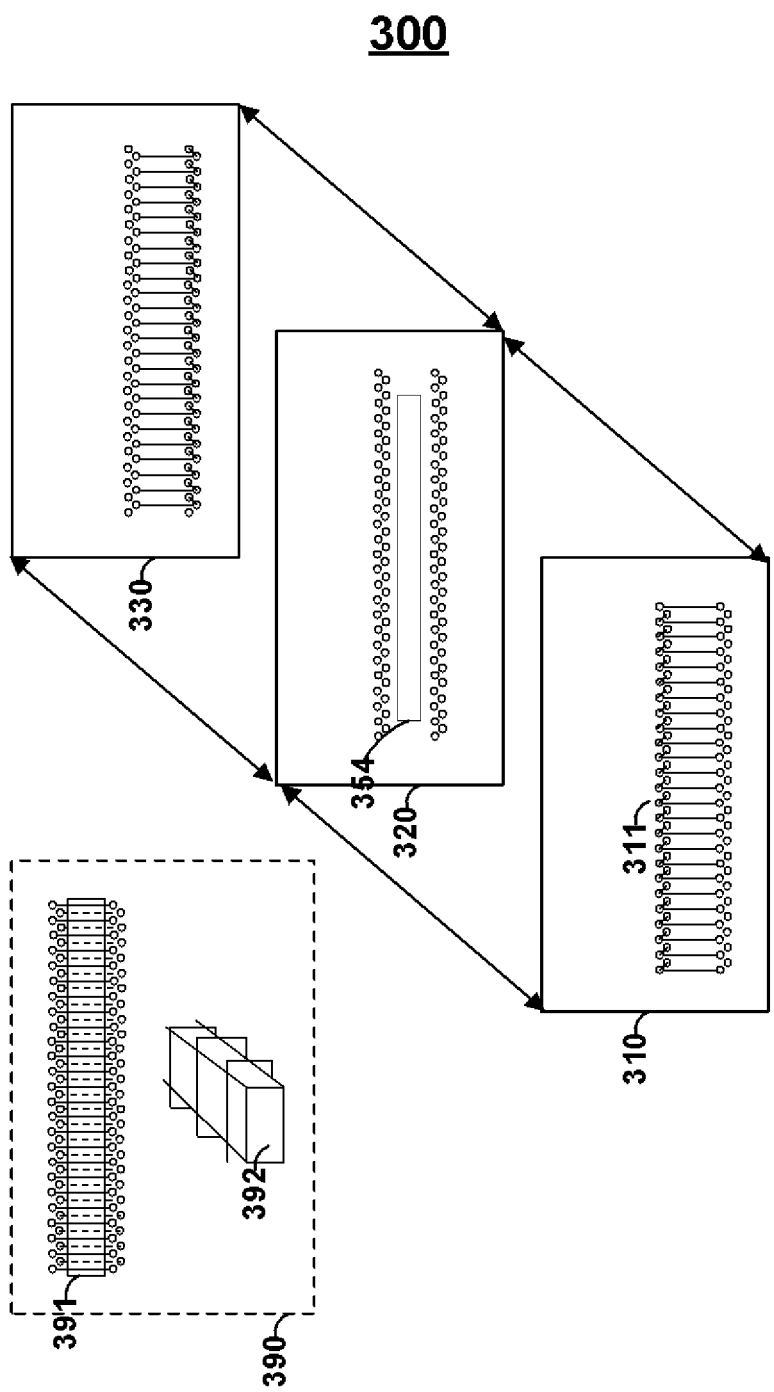
FIG. 3 is an illustration of a card constructed in accordance with the principles of the present invention.

FIG. 3 shows fabrication process 300, in which layer 310, 320, and 330 are attached together. Layer 310 may include a set of coil segments that are coupled to a set of coil segments on layer 330 to form a coil. Layer 320 may include material 354 to assist in manipulating the electromagnetic field generated by the coil. Vias may be placed on layer 320 such that the coil segments from layer 310 may be coupled to the coil segments from layer 330. Layers may be, for example, layers of a flexible or rigid material such as an FR4 epoxy dielectric. Coil 390 may be formed from such a process that may include top view 391 and cross-sectional view 392.

Figure 4:
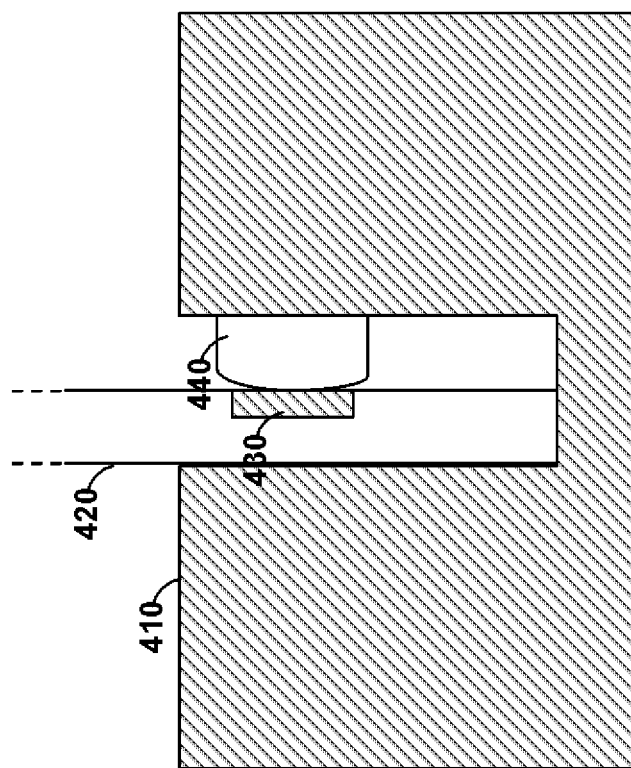
FIG. 4 is an illustration of a card and a reader constructed in accordance with the principles of the present invention.

FIG. 4 shows environment 400 that may include magnetic stripe reader 410, read-head housing 440, card 420, and magnetic emulator 430. Read-head housing 440 may include any number of read-head's such as, for example, one, two, or three read-heads. Each read-head may independently receive magnetic fields from magnetic emulator 430 (or a magnetic stripe, such as a magnetic stripe encoded on-card by card 420). Emulator 430 may be positioned to be adjacent to any one or more read-heads of read-head housing 440 or may be positioned to communicate information to any one or more read-heads of read-head housing 440. Persons skilled in the art will appreciate that emulators with longer lengths may be located within the proximity of one or more read-heads for a longer duration of time when a card is swiped. In doing so, for example, more information may be transmitted from an emulator to a read-head when a card is being swiped.

Figure 5:
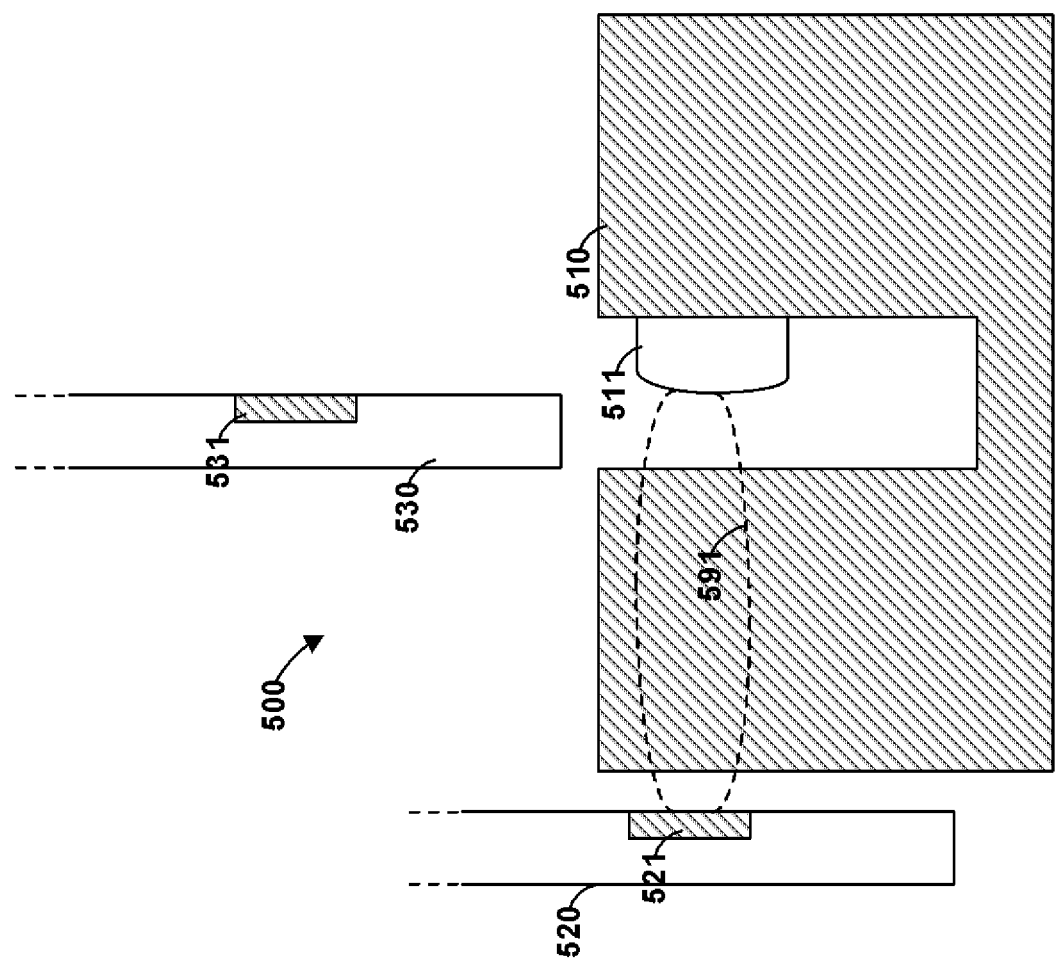
FIG. 5 is an illustration of a card and a reader constructed in accordance with the principles of the present invention.

FIG. 5 includes environment 500 that may include cards 520 and 530 as well as magnetic stripe reader 510. Read-head housing 511 may be included on a wall of a trough of magnetic stripe reader 510. The trough may be sized to accept cards (e.g., credit cards).

Card 520 may include emulator 521. Emulator 521 may provide electromagnetic field 591 that may transmit through a portion of the housing of magnetic stripe reader 510 (e.g., through a wall of a trough to get to read-head housing 511). Accordingly, card 520 may be located outside of a reader—yet still be operable to communicate information to a magnetic stripe reader. A reader may be provided with an outer wall, for example, with a thickness of a quarter of an inch or more. Emulator 521 can provide electromagnetic field 591 over a distance of, for example, a quarter of an inch or more.

Persons skilled in the art will appreciate that card 520 may be coupled to a device via a permanent or removable cable. Such a device may provide power to card 520 as well as control information—such as control information for emulator 530. An external source of power may be utilized, for example, to provide a larger amount of electrical energy to emulator 521 than from a source of power located within card 520. Persons skilled in the art will appreciate that a car having an internal battery may still be able to receive a cable from a device having its own source of electrical energy.

Card 530 may be provided with emulator 531 and may electrically couple with a read-head of magnetic stripe reader 510. Any number of emulators may be provided in card 530 in any number of orientations such that the appropriate electromagnetic field may couple with a read head of read-head housing 511 regardless of the orientation of card 720 with respect to read-head 511. More particularly, for example, additional read-head housings may be provided in magnetic stripe reader 510 at different locations about the reader to electrically couple with a emulators in a number of different configurations. A sticker and/or guide-structures may be provided on a magnetic stripe reader to, for example, direct a user on how to position his/her card (or other device) for contactless transmission of data (e.g., credit card data) to a read-head housing without using the trough that includes that read-head housing.

Persons skilled in the art will appreciate that a magnetic stripe reader may include a trough that includes two (or more) read-head housings 511 located in approximately the same vertical position on a card-swiping trough, but at different horizontal locations on opposite walls of the trough. In doing so, for example, a magnetic stripe may be read regardless of the direction that a card having the magnetic stripe is facing when the card is swiped. Magnetic emulator 521 may, for example, communicate magnetic fields outside both the front and read surfaces of a card. Accordingly, a single emulator 521 may, for example, couple with a single read-head regardless of the direction the card was facing when swiped. In doing so, for example, the costs of readers may be reduced as only a single read-head may be need to receive information regardless of the direction a card is facing when swiped. Accordingly, magnetic readers do not need stickers and/or indicia to show a user the correct orientation to swipe a card through a magnetic stripe reader. An adapter may be provided that coupled directly to a read-head that allows a device not operable to fit in a trough to electrically couple with a read-head.

An emulator may be positioned about a surface of a card (or other device), beneath a surface of a device, or centered within a card. The orientation of a magnetic emulator in a card may provide different magnetic fields (e.g., different strength's of magnetic fields) outside different surfaces of a card. Persons skilled in the art will appreciate that a magnetic emulator may be printed via PCB printing. A card may include multiple flexible PCB layers and may be laminated to form a card using, for example, a hot and/or cold lamination. Portions of an electronic ink display may also be fabricated on a layer during a PCB printing process.

Persons skilled in the art will appreciate that a number does not need to, for example, change with time. Information can change, for example, based on manual input (e.g., a button press or combination of button presses). Additionally, a credit card number may be a static display number and may be wholly or partially displayed by a display. Such a static credit card number may result in the reduction of fraud if, for example, a personal identification code is required to be entered on a manual input entry system to activate the display. Additionally, fraud associated with card cloning may be minimized with the use of a magnetic emulator activated by the correct entry on a manual input entry system.

Person skilled in the art will also appreciate that a card may be cloned by a thief, for example, when the thief puts a illegitimate credit card reader before a legitimate credit card reader and disguising the illegitimate credit card reader. Thus, a read-head detector may detect a read-head housing and then, if a second read-head housing is detected on the same side of the credit card, the reader may transmit information to the second read-head that signifies that two read-head housings were detected. In doing so, for example, a bank, or the police, may be notified of the possibility of the presence of a disguised cloning device. The information representative of multiple read-heads may be included with information that would allow a credit card number to be validated. As such, a server may keep track of the number of read-head housings at each reader and, if more read-head housings are detected than expected, the server may contact an administrator (or the police). The server may also cause the credit card transaction to process or may reject the credit card transaction. If the number of read-head housings (or read-heads) is the number expected by the server, the server can validate the payment transaction.

A payment system using dynamic numbers may, for example, be operable with numbers that are stored outside of the period in which those numbers would otherwise be valid. A server may be included, for example, that accepts a dynamic credit card number, information representative of a past credit card number, and the merchant that is requesting payment. The server may register that merchant for that saved number. The number may be decrypted (or otherwise validated) for that past period of time. Accordingly, the credit card transaction may be validated. Additionally, the merchant identification information may be linked to the stored dynamic credit card number for that past period of time. If the server receives a transaction from a different merchant with that same dynamic credit card number for that same period of time, the server may reject the transaction. In doing so, a merchant may be protected from having credit card numbers stolen from its various storage devices. If a thief steals a number from a merchant's server that is associated with a past period of time, that number cannot be used, for example, anywhere else. Furthermore, such a topology may, for example, allow merchants to provide a one-click shopping, periodic billing, or any other type of feature that may utilize dynamic numbers that are stored and used outside of the period in which the dynamic numbers were generated.

Persons skilled in the art will appreciate that different emulators may be controlled by different switching circuitry (e.g., different transistors).

Persons skilled in the art will appreciate that multiple buttons may be coupled together to form a single-bit bus. If any button is pressed, the bus may change states and signal to the processor to utilize different ports to determine what button was pressed. In this manner, buttons may be coupled to non-triggerable ports of a processor. Each button (or a subset of buttons) may be coupled to one or more triggerable ports of a processor. A port on a microprocessor may be utilized to drive an emulator in addition to, for example, receiving information from a button. For example, once an appropriate personal identification code is received by a processor, the processor may utilize one or more ports that receive information from one or more buttons to drive an emulator (e.g., for a period of time). Alternatively, for example, a magnetic emulator may be coupled to its own triggerable or non-triggerable processor port. A card may also include a voltage regulator to, for example, regulate power received from an internal or external source of power.

Persons skilled in the art will appreciate that any type of device may be utilized to provide dynamic magnetic information on a card to a magnetic stripe reader. As discussed above, a magnetic encoder may be provided that can change information on a magnetic medium where the changed information can be detected by a magnetic stripe reader.

Figure 6:
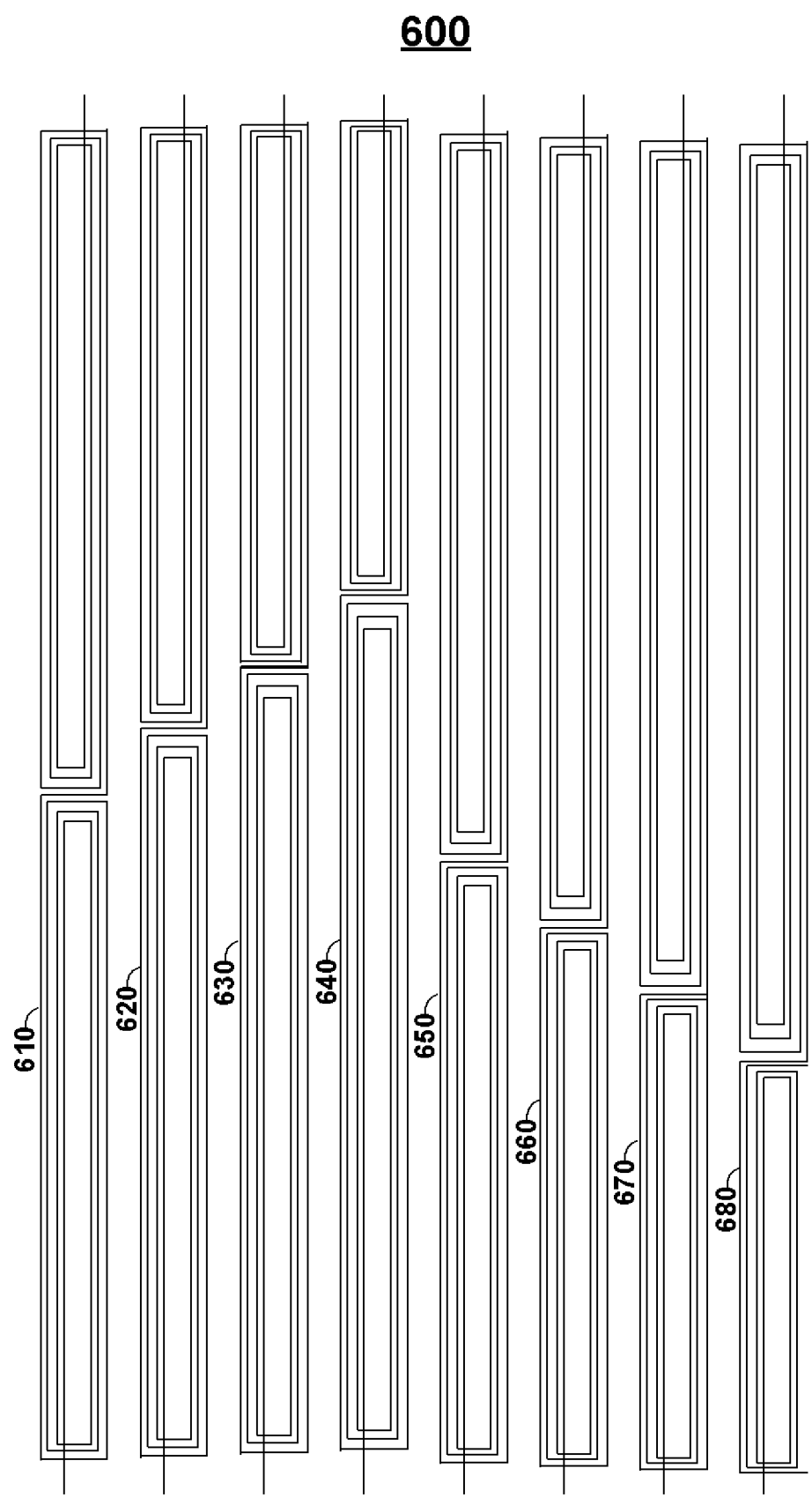
FIG. 6 is an illustration of a circuit constructed in accordance with the principles of the present invention.

FIG. 6 includes topology 600 that may be utilized to communicate information to a read-head. Topology 600 may include magnetic emulators 610, 620, 630, 640, 650, 660, 670, and 680. Each of these magnetic emulators may be provided on a different layer and aligned such that the primary paths are seen, from the perspective of a read-head as one set of paths. The return paths may be aligned to minimize the amount of time a read-head is located above the return paths of the magnetic emulators. The magnetic emulators may be coupled in series or operated independently. Additional layers may be included to include additional routing between the magnetic emulators. A magnetic emulator may be, for example, a flat coil placed on a single layer of material. Current may be provided through a magnetic emulator such that the magnetic emulator generates an electromagnetic signal. A primary path of a coil may include a dense section of coil segments where current runs through those coil segments in the same direction. Accordingly, the electromagnetic field is intensified in active region compared to the area of the coil with coil segments that are widely spaced or not configured in an orientation where the magnetic fields from these coil segments can be read. Accordingly, a current may be placed through the coil such that a magnetic stripe reader is operable to receive information from active region 651 but not the region outside active region 651. Persons skilled in the art will appreciate that the direction of current through magnetic circuit 650 may be changed and controlled in a pattern that is representative of magnetic stripe data. Particularly, a processor may, for example, transmit information through a coil by changing the direction of the electromagnetic field generated from emulator circuit at particular times. A change in the frequency of field reversals may be representative of, for example, a particular bit of information (e.g., "1" or "0"). Magnetic emulation circuit 650 may include a dense active region and a less dense return paths. A magnetic emulation circuit may include return paths that also can transmit information to a read-head, but that provides an electromagnetic field in an opposite direction to that of a primary path. Accordingly, read-head sensors may be placed, for example, such that no current is provided through a magnetic emulator while a read-head is over a return path, but the emulator is utilized to communicate information when the read-head (or read-heads are located over the primary path). Additionally, a processor may change how an emulator is controlled in order to accommodate the different electromagnetic fields produced by the two regions such that a portion of a set of data can be transmitted by a return path and a portion of the set of data can be transmitted by a primary path. If zones, for example, are implemented, the return path may be utilized to communicate a portion of information when that zone associated with the return path is utilized and primary paths may be utilized to communicate another portion of information the zone associated with the primary path is activated. Accordingly, return paths may be staggered in order to increase their total visibility to a read-head. Magnetic emulators 610, 620, 630, 640, 650, 660, 670, 680, and 680 may be sized to fit, for example, within the footprint of a track of data for a payment card. The primary paths of these magnetic emulators may be staggered such that, from above, a continuous set of primary path segments is seen. Accordingly, the emulators may be controlled in the same way such that, for example, a continuous electromagnetic field is produced and can be controlled. Accordingly, data can be communicated serially through this continuous electromagnetic field to a magnetic stripe reader. An instance of topology 600 may, for example, be provided for each track of information on a magnetic card. Different magnetic emulator topologies may be utilized for different tracks. Different magnetic emulators in a magnetic emulator topology may be provided different amounts of current such that emulators at different depths can provide a sufficient electromagnetic field at the surface of topology 600.

Figure 7:
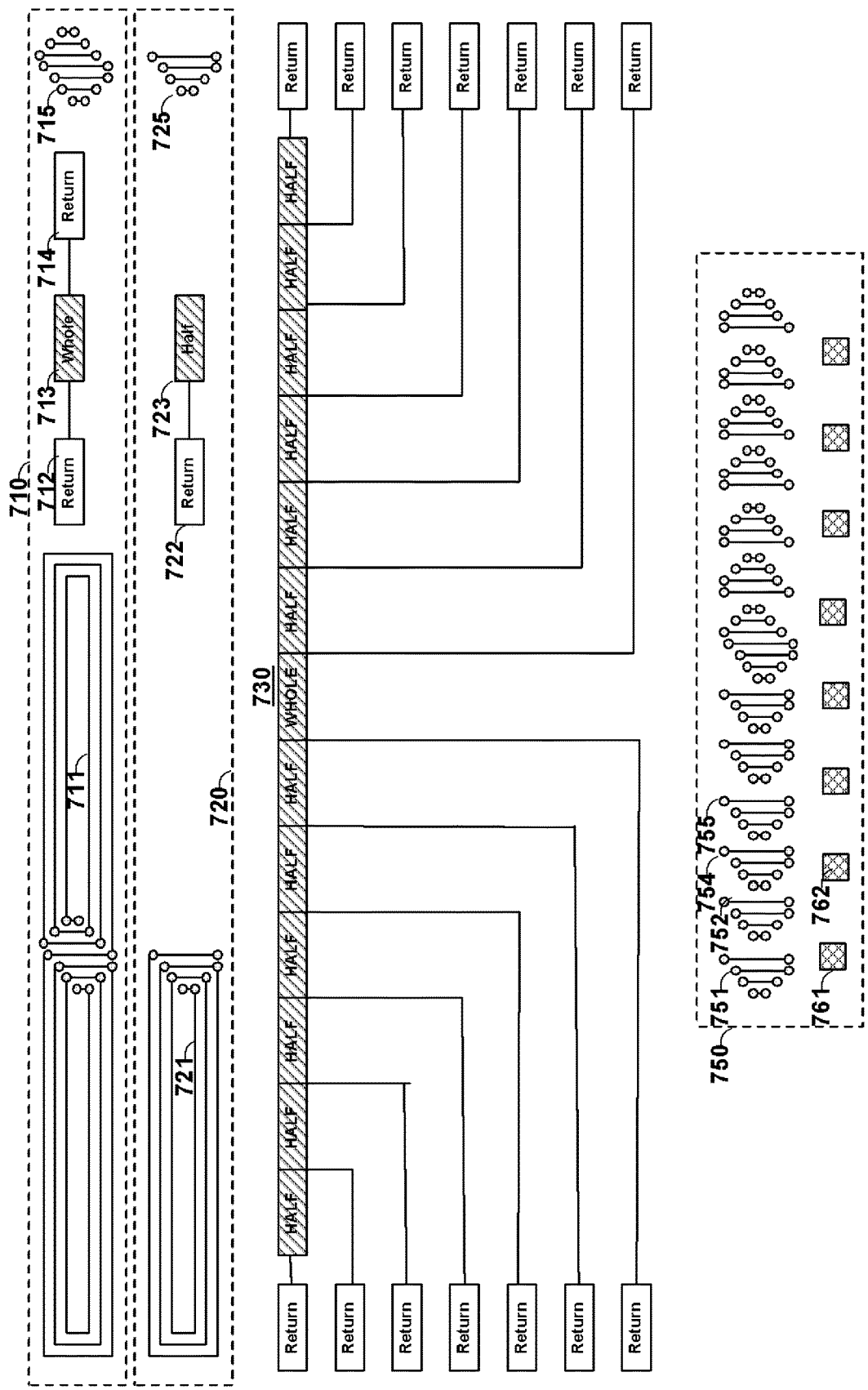
FIG. 7 is an illustration of a circuit constructed in accordance with the principles of the present invention.

FIG. 7 shows topology 700 where the primary paths of multiple emulators are provided on a layer of material and the return paths for the coils that are included in those emulators are provided on different layers. Accordingly, for example, each emulator may be provided with the same amount of current to produce a sufficient electromagnetic field. Such coils may be, for example, flat coils that are bent onto multiple layers (e.g., utilizing vias).

Topology 700 may include coil 711 with two portions of return paths and one portion of primary paths that may be, for example, visualized as return portion 712, primary portion 713, and return portion 714. The primary portion may be viewed from an eagle-eye perspective as portion 715. Multiple emulator design 730 is included that may include multiple emulators with primary paths located adjacent to one another to provide a continuous electromagnetic field. The emulators may be controlled independently such that different emulators are utilized to communicate information at different times. Accordingly, emulators may be utilized from left-to-right as a reader passes over the emulators from left-to-right. For example, read-head detector 761 of circuit 750 may detect the presence of a read-head (e.g., a housing that stores a read-head) and may signal the processor to communicate with emulators 751 and 752. When read-head detector 762 detects the presence of the read-head, read-head detector 762 may signal the processor to communicate with emulators 752, 754, and 755. Read-head detectors 761 and 762 may be, for example, contacts coupled to a capacitive sensing circuit or different capacitive sensing circuits.

Figure 8:
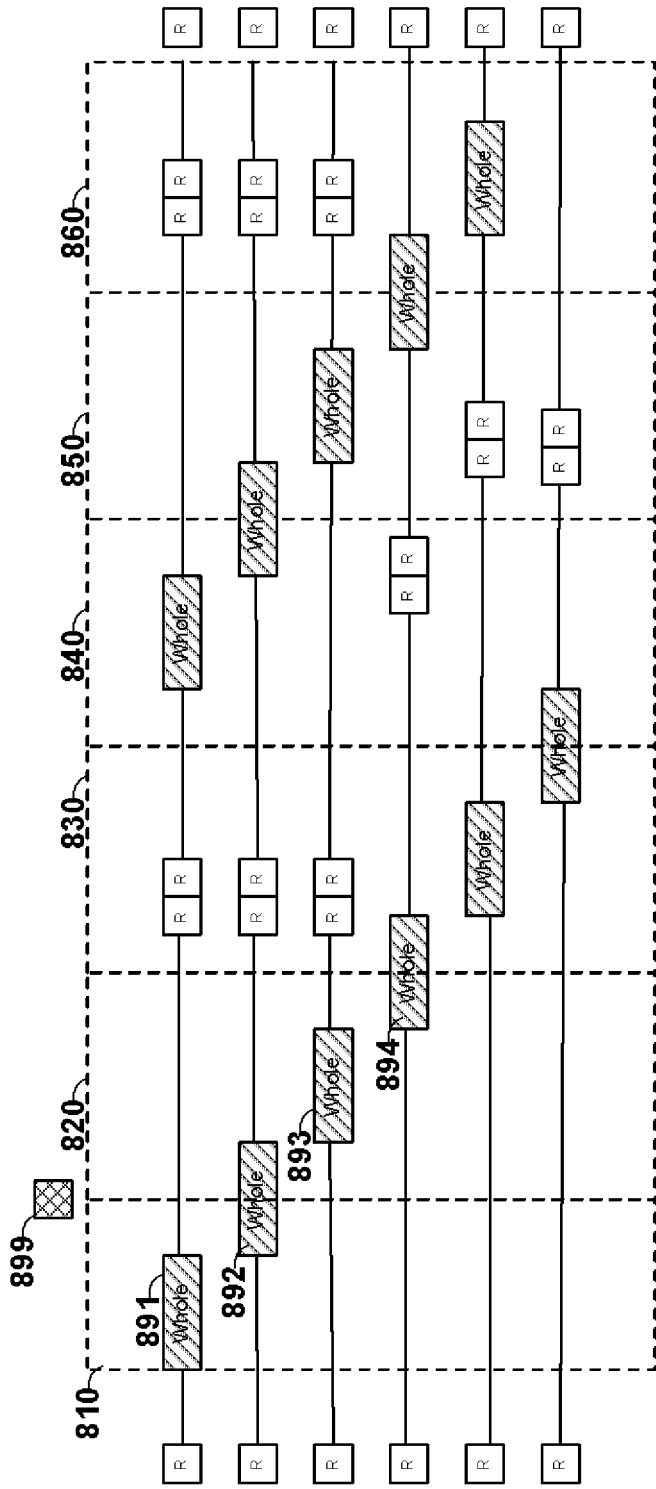
FIG. 8 is an illustration of a circuit constructed in accordance with the principles of the present invention.

FIG. 8 shows topology 800 that may include, for example, zones 810, 820, 830, 840, 850, and 860. Topology 800 may be a cross-sectional perspective of a multiple layer card. Primary paths 891 and 892 may, for example, be located in zone 810 and primary paths 892, 893, and 894 may be located in zone 820. Primary path 892 may be utilized, for example, to produce a transitional electromagnetic field between zones 810 and 820. Read-head detector 899, for example, may be utilized to signal the processor to change from operating zone 810 to operating zone 820 to communicate data. Primary portions may be divided into more than one primary portion and placed in different zones such that an emulator that includes a coil having two primary portion may cover more than one zone as well as non-adjacent zones. Similarly, return paths portions may be utilized to communicate data and primary portions may not be utilized (e.g., using a zone-based control methodology).

Figure 9:
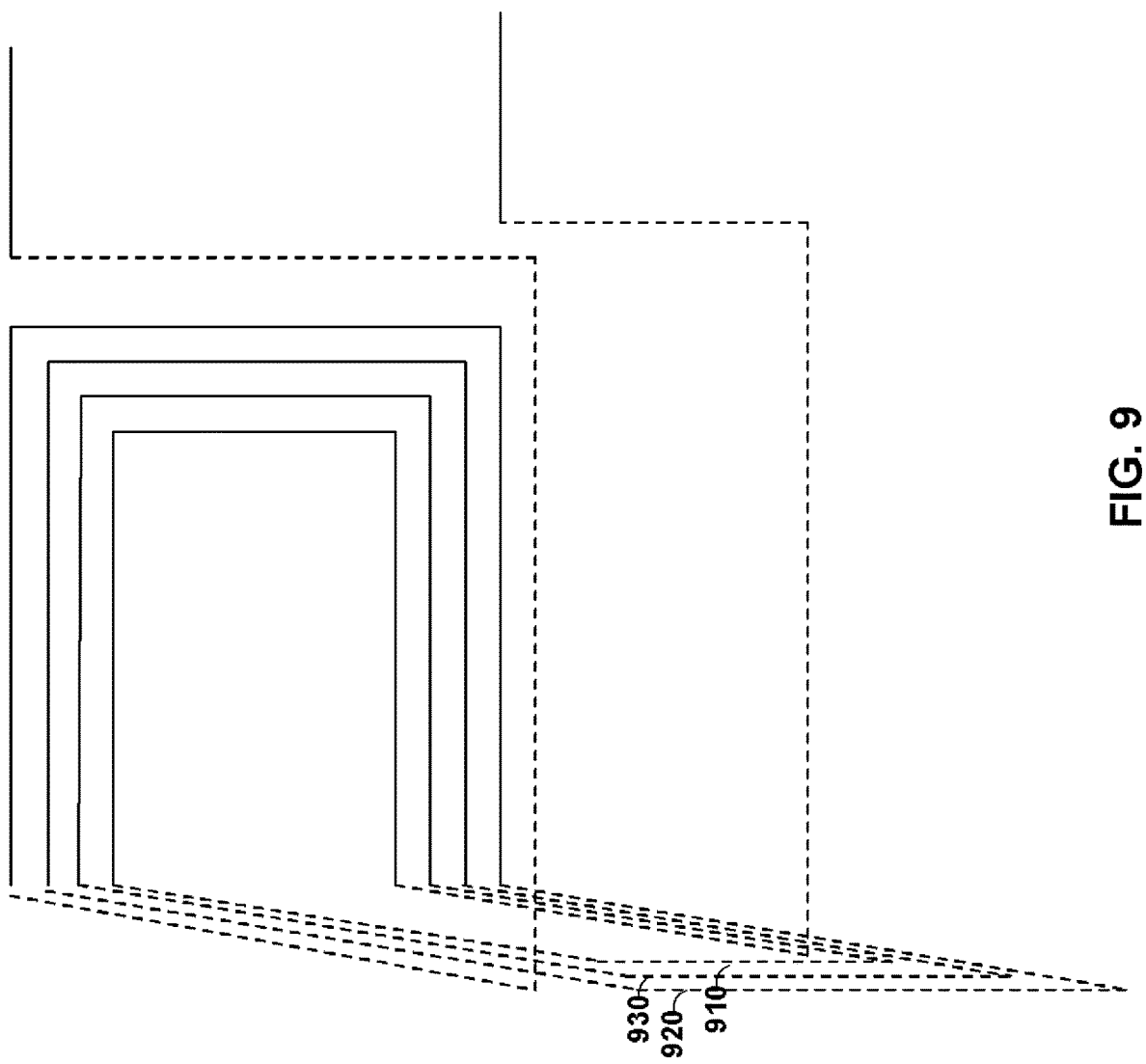
FIG. 9 is an illustration of a circuit constructed in accordance with the principles of the present invention.

FIG. 9 shows circuit 900 that may include primary paths on one layer, but that may place a different return path on different vertical layers such that the return paths are vertically stacked. In doing so, the area of the return paths (as viewed by a read-head) may be minimized. In a zone-based control topology, minimizing the read-head visibility to the return paths may, for example, allow for a layer margin of error when detecting the location of a read-head. Circuit 900 may include return paths 910, 920, and 930.

Figure 10:
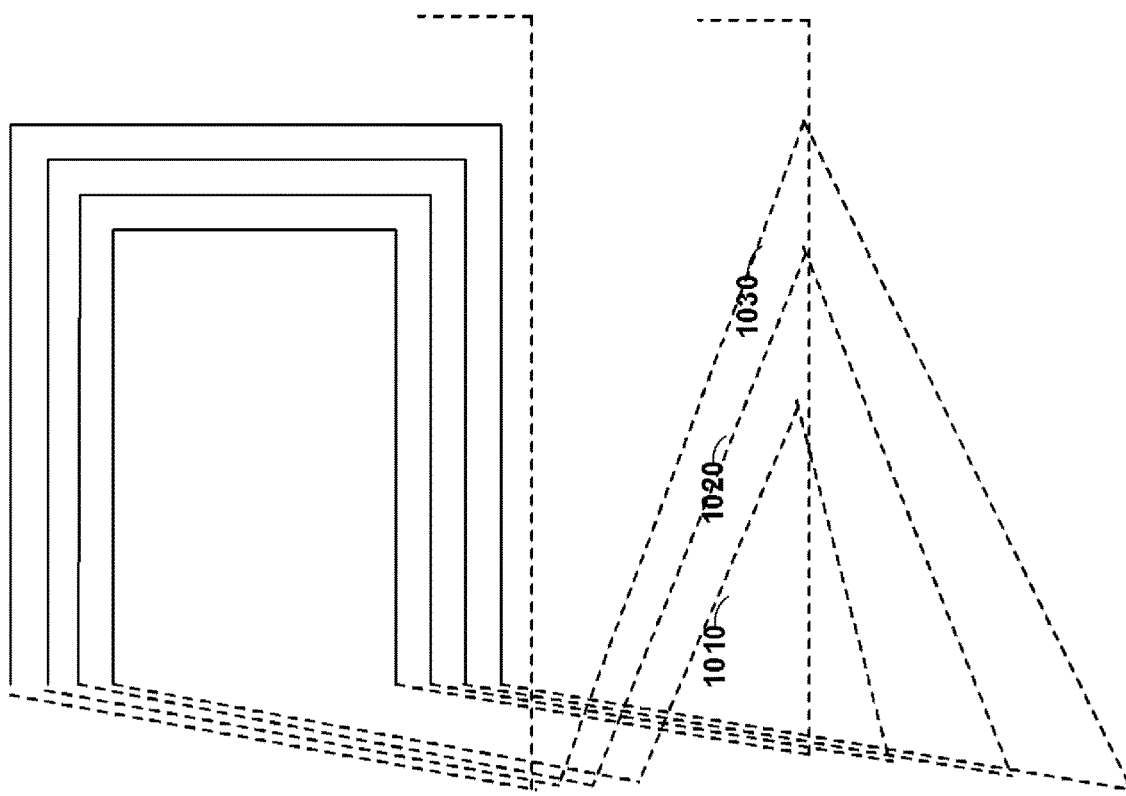
FIG. 10 is an illustration of a circuit constructed in accordance with the principles of the present invention.

FIG. 10 includes circuit 1000 that may include, for example, a return portion that forms a triangle such that a return path includes two segments that are angled from one another. Each segment may be at a 45 degree angle from a path (e.g., a path it is vertically aligned with) and the two may be, for example, at a 90 degree angle from one another. One or more materials may be placed between the primary paths and the return paths either from the perspective of going into the page or spanning the length of the page (e.g., threading through the open loop created by the primary and return paths). Circuit 1000 may include return paths 1010, 1020, and 1030.

Figure 11:
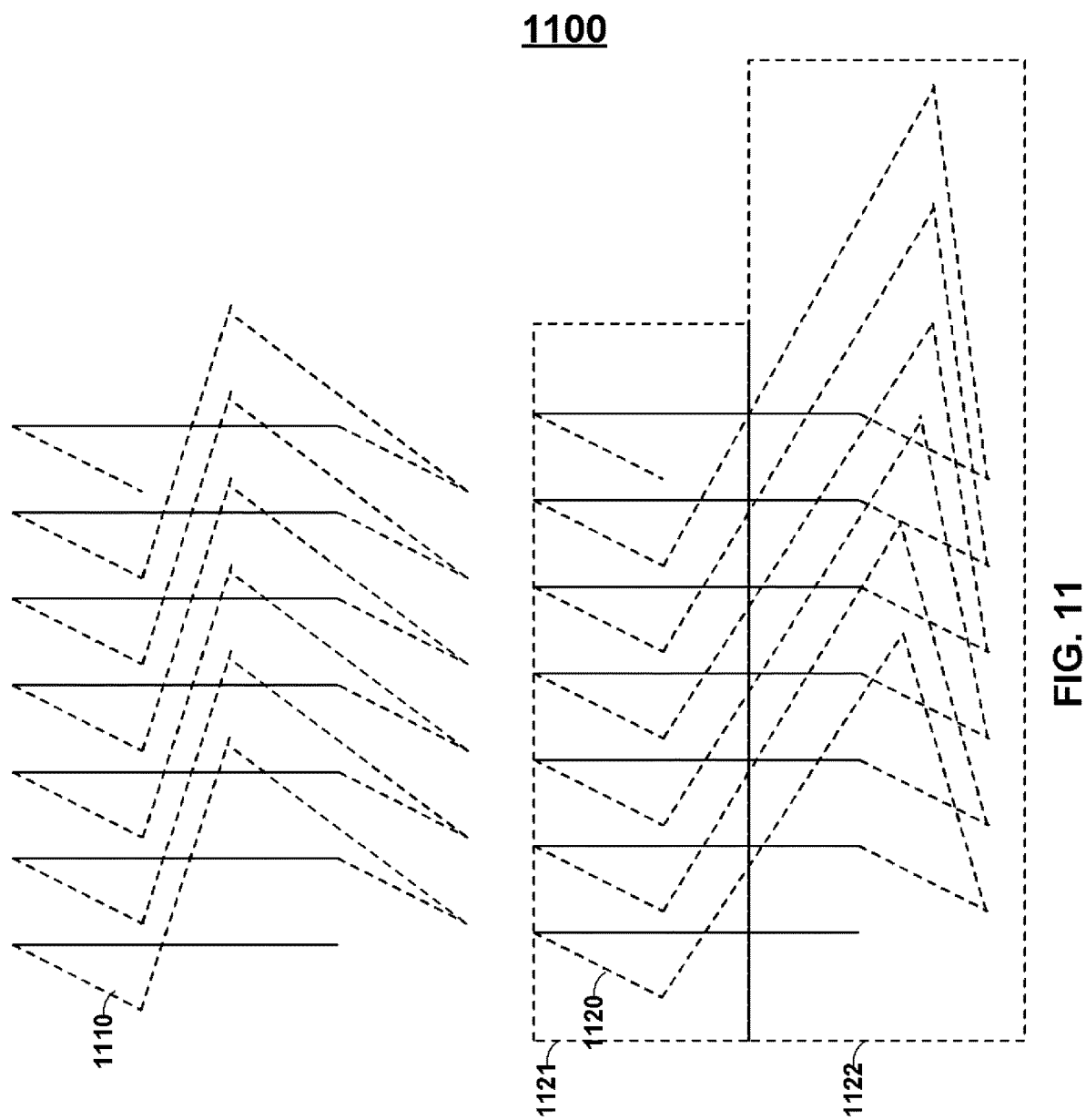
FIG. 11 is an illustration of a circuit constructed in accordance with the principles of the present invention.
Figure 12:
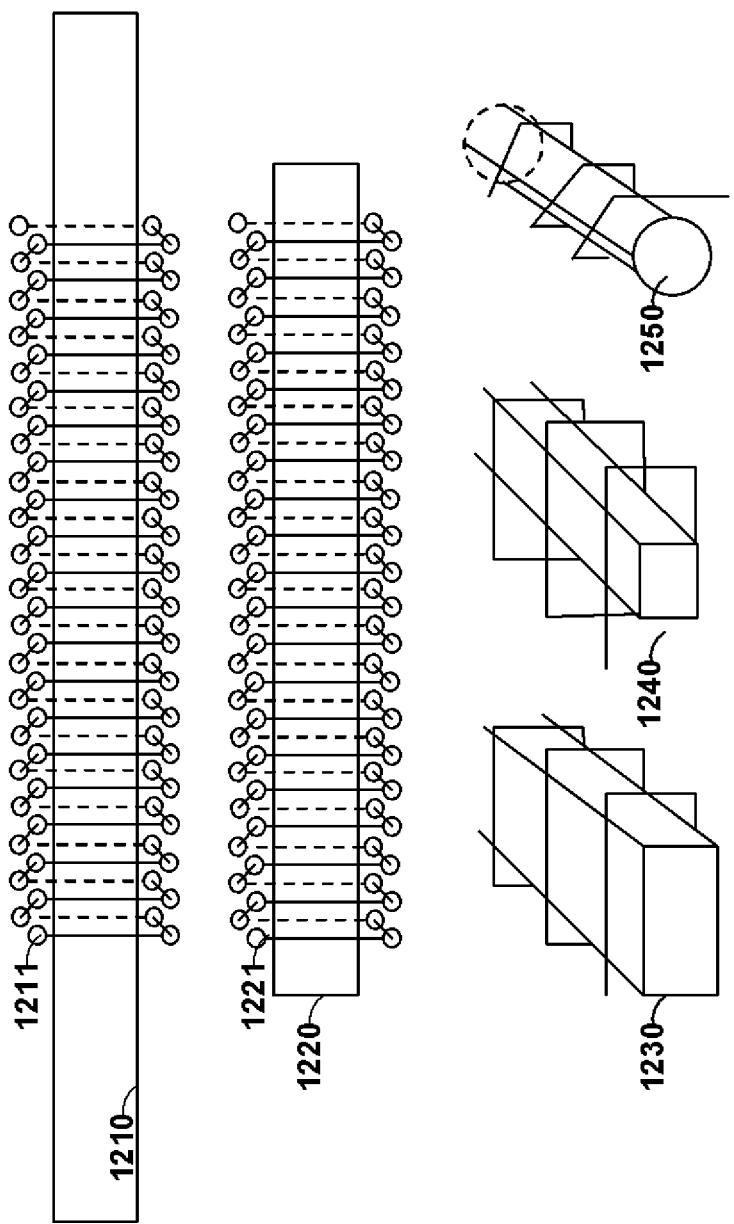
FIG. 12 is an illustration of a circuit constructed in accordance with the principles of the present invention.

FIG. 11 includes circuit 1110 that may be, for example, a coil. Circuit 1120 may be included that includes two angled return path segments that are located in area 1222, which is outside track footprint 1121. Area 1122 may correspond to an area, for example, that is outside of where a read-head (or read-head housing) passes.

FIG. 1200 shows coil 111 that may include interior material 1210. Multiple pieces of interior material 1210 may be provided inside of coil 1211. Interior material 1210 may be, for example, a magnetic, ferromagnetic, and/or a ferromagnetic material. A powder may be utilized. An alloy may be utilized. An interior material may extend various distances outside of a coil. An interior material may end at the last coil segment of a coil. Coil 1221 includes interior segment 1220.

A coil may be wrapped around interior materials of different shapes and sizes. A gap between a coil may be provided having various distances. A material may be provided between the interior material and the coil such that the interior material does not, for example, short the coil. An interior material may be, for example, rectangular (e.g., material 1230), square (e.g., material 1240), or cylindrical (e.g., material 1250).

FIG. 13 shows card 1300 that may include, for example, processor 1320, display 1340, switching circuitry 1330, read-head detectors 1350 and 1360, and coils 1370, 1380, and 1385. Coils 1370, 1380, and 1385 may span the length of a track and may communicate information serially. Coils 1370, 1380, and 1385 may be spaced and controlled such that the electromagnetic field from one coil does not introduce interference in a read-head attempting to read information from another track (e.g., an adjacent track). An interior material may be provided to assist in manipulating the profile of the electromagnetic field provided by a coil.

A read head detector may include a cluster of read-head detectors such as cluster 1390. Cluster 1390 may include read-head detectors 1391-1399. Each read-head detector may be, for example, a capacitive sensor. The read-head detectors may thus, for example, be conductive areas coupled to a capacitive sensing circuit. Cluster 1390 may be coupled to a multi-channel capacitive sensing circuit. Each of the contacts of a cluster may be coupled to their own capacitive sensing circuit. A microprocessor may be utilized in capacitive sensing. Any type of read-head detector may be utilized in cluster 1390. For example, a read-head detector may include a physical contact, proximity, optical, or other detector. A cluster may include multiple different types of read-head detectors. Cluster 1390 may be utilized to discern, for example, between different objects. For example, a processor may determine that a user swiped the card through a reader if, for example, 1) only read-head detector 1396 detects an object; 2) after read-head detector 1396 detects an object, only read-head detector 1395 detects an object; and 3) after read-head detector 1395 detects an object, only read-head detector 1394 detects an object. Accordingly, different detection profiles can be associated with readers such that if other types of objects are detected, the processor can discern between these objects and read-heads. Different profiles may be associated with different readers (e.g., motorized, insertion-swipe, and user-swipe). Such different profiles may be utilized to better combat card cloning as, for example, a fake reader overlaid on top of a legitimate ATM machine may have a different profile.

Persons skilled in the art will appreciate that a magnetic emulation circuit may act as a read-head detector as well as a magnetic information transmitter. For example, a magnetic emulator may be driven according to a process that includes a step in which a correct Personal Identification Code (e.g., a PIN) is determined to have been entered on a card. Accordingly, another step may activate, in which a coil is driven such that its return paths act as a read-head detector. This may be done in numerous ways. For example, the current providing an electromagnetic field may undergo a phase-shift when a magnetic and/or conductive material is placed in the electromagnetic field. Accordingly, a phase-shift may be determined. When such a phase-shift is determined, a step may initiate and a magnetic emulation circuit may be driven to communicate data serially. Accordingly, some region(s) may be utilized to detect a read-head and other region(s) 1220 may be utilized to communicate information to that read-head. Persons skilled in the art will appreciate that a magnetic emulation circuit may not be supplied current until an appropriate Personal Identification Code (PIC) is entered into manual interfaces located on the card. Such a scheme, for example, provides for power savings as well as prevents card cloning. Accordingly, a magnetic emulator may be driven into a read-head detector mode upon receiving an appropriate manual input and then into a data transmission mode after determining the presence of a read-head.

Figure 14:
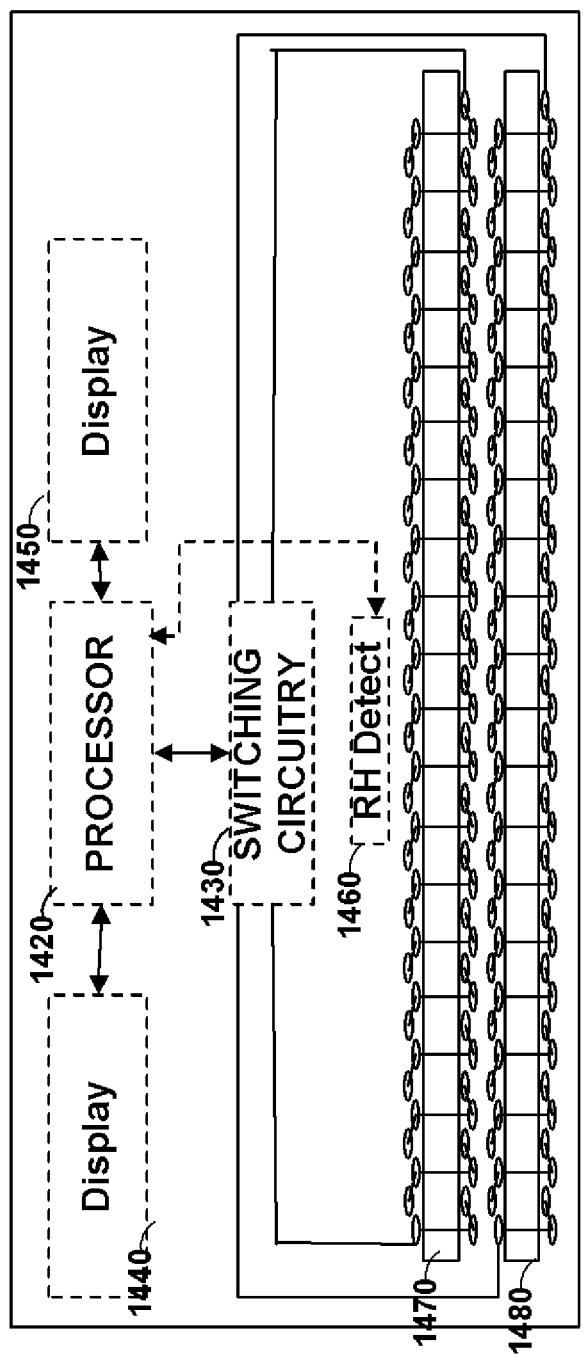
FIG. 14 is an illustration of a card constructed in accordance with the principles of the present invention.

FIG. 14 shows card 1400 that may include display 1440, processor 1420, display 1450, switching circuitry 1430, emulators 1470 and 1480, and read-head detector 1460. Read-head detector 1460 may be located such that emulators are located between read-head detector 1460 and an edge of the card. Accordingly, for example, a read-head detector may be triggered when a read-head is in the middle of the card such that a single read-head detector can be utilized. Data may be communicated quickly such that all data is transmitted serially before a read-head (or read-heads) travel past emulators 470 and 480. Additionally, a capacitive sensing circuit may be coupled to detector 1460 without having the interconnection fall within the path of a moving read-head. In doing so, capacitive changes in the interconnection due to a read-head moving over an interconnection may not mis-trigger a capacitive sensing circuit.

Persons skilled in the art will appreciate that a user's payment card number (e.g., credit card or debit card number) does not have to change. A display may hide this payment card number until an appropriate unlocking code is entered into buttons of the card. Similarly, a magnetic emulator may not be provided current until the proper unlocking code is entered—thus keeping magnetic information private and not allowing undesirable readers to read a card. A security code may be displayed on the same or a different display. A button may be provided representative of an online purchase (or a user may utilize buttons to instruct the processor that an online purchase is desirable). For such an online purchase, the credit card number and the security code may be displayed—but the magnetic emulator may not be activated. In doing so, the level of security of the card is increased. Furthermore, for example, a button may be provided representative of in-store purchases (or a user may utilize buttons to instruct the processor that an in-store purchase is desirable). Accordingly, a processor may be signaled that an in-store purchase is desired. A different operation may be associated with different types of purchases (e.g., online or in-store). Accordingly, for example, magnetic emulators may be activated for an in-store environment—but not the displays. Accordingly, for example, a restaurant cashier may not be able to read the credit card number from the card, but may still be able to swipe the card. If a reader is down or a cashier requires reading particular information (e.g., a security code or credit card number information) then controls may be utilized to communicate this information. A record of the types of transactions may be stored and may be communicated in discretionary fields of data within a transmitted data track. Such record information may be utilized, for example, to further increase security and/or introduce a variety of additional functionality.

Different types of cards may be provided on a card. For example, a security ID number and a credit card number may both be provided on the same card. A button may be utilized to allow a user to provide instruction to a processor such that the processor can display (e.g., visually and/or magnetically) the desired information. For example, a user may determine to use one of a variety of payment accounts (e.g., credit and/or debit) for a purchase. An entire payment number (e.g., credit or debit) may be changed and/or hidden visually and/or magnetically. A portion of a payment card number (e.g., credit or debit) may be changed and/or hidden visually and/or magnetically.

Persons skilled in the art will appreciate that a display on the card may display a credit card number that does not change with time. Additionally, for example, a magnetic emulator (or multiple magnetic emulators) may magnetically communicate financial data that does not change with time. Such a card may reduce, for example, the effects of physical card theft and card cloning.

One or more light generation devices, such as a Light Emitting Diode (LED), may be provided as part of a card (or other device). Such an LED may produce light, for example, upon a manual input such as a button press, the correct entry of a PIC such as a PIN, and/or the incorrect entry of a PIC. A light emitting device may be operable to produce different colors of light. For example, the incorrect entry of a PIC may produce a red light and the correct entry of a PIC may produce a green light. A PIC may take any form such as a numerical code or a code that include alphabet letters and/or symbols. For example, a PIC may be "A-B-B-B-A" and an "A" button may be provided on a card in addition to a "B" button (as well as other buttons such as a "C," "D," and/or "E" buttons).

Persons skilled in the art will appreciate that any numbers of a credit card number may remain static and/or change either with time or based off a transaction (e.g., by sensing a read-head "swipe"). Additionally, any static and/or dynamic numbers may be displayed via a display or printed on a card. For example, a middle 6 digits of a credit/debit card number may be static and may be displayed on a display. Such a middle 6 digits may be displayed, for example, upon the entry of a correct PIC. Similarly, a magnetic emulator may not communicate information until a correct PIC has been entered by a user. Doing so may, for example, reduce fraud associated with card cloning. Additionally, a receipt may be provided that includes masked credit card numbers except for the last few digits of credit card numbers. Accordingly, displaying a static middle 6 digits of credit card numbers may allow for such a receipt to be provided while still reducing credit card fraud from hiding numbers that are not displayed on such a receipt. Any amount of numbers and/or characters may be displayed through a display. For example, nineteen digits may be displayed as part of a credit/debit numbers and these numbers may also be communicated through one or more magnetic emulation circuits. The entry of particular PICs may provide different results. For example, a first PIC may only display a string of alphanumeric characters. A second PIC may only activate a magnetic emulation circuit to transmit information including that string of alphanumeric characters (or a different string). A third PIC may activate a magnetic emulation circuit and a display. A display and/or magnetic emulation circuit may be turned OFF, for example, upon entry of an incorrect PIC and/or after a period of time has passed since the entry of the PIC and/or after the detection of a particular number of swipes by a read-head detector (e.g., one or two).

Persons skilled in the art will appreciate that a credit/debit card number (or any other information) may remain static until an event occurs and then may become dynamic (e.g., change based on swipes and/or time). For example, a particular PIC may change from a static to a dynamic topology and/or a topology may be changed from static to dynamic after a pre-determined period of time. Additionally a card and/or device may include a wireless receiver and a topology may be changed from a static to a dynamic topology upon, for example, receiving an appropriate signal from the wireless receiver. Accordingly, a validation process may change at a validation server depending upon whether a card is utilizing a static and/or dynamic topology at any given time. Additionally, a static credit/debit card number may be printed on the face of a card and information (e.g., a security code) may be displayed via a display and remain static over time (or with use) or be provided dynamically.

A card or other device (e.g., a mobile telephone) may accept a pre-determined number of consecutive incorrect PICs before locking the card for a period of time or until an appropriate secondary PIC is entered. Accordingly, a user may enter in an incorrect PIC a number of times and then, after a card becomes locked, call a support center for a secondary one-time use PIC. A card may cycle through unlocking PICs based, for example, on time or the number of previous unlock attempts.

A website may be provided where a user enters in his/her credit card number, pays a fee, and a new card is programmed and sent to the user. The new card may include a display to display a portion of the users credit/debit card number in a static form upon entry of an appropriate PIC. Such a card may also include one or more magnetic emulation circuits to transmit the information to a reader. Such a card may or may not, for example, include a portion of a magnetic stripe. For example, three tracks of magnetic stripe data may be communicated via three different emulation circuits, more than three different emulation circuits, one emulation circuits (e.g., tracks communicated serially to all read-heads), or one or more tracks may be represented by magnetic stripe(s) while one or more other tracks may be represented by a magnetic emulation circuit. A track of data may also be partially represented by a magnetic emulation circuit and partially represented by a magnetic stripe.

Figure 15:
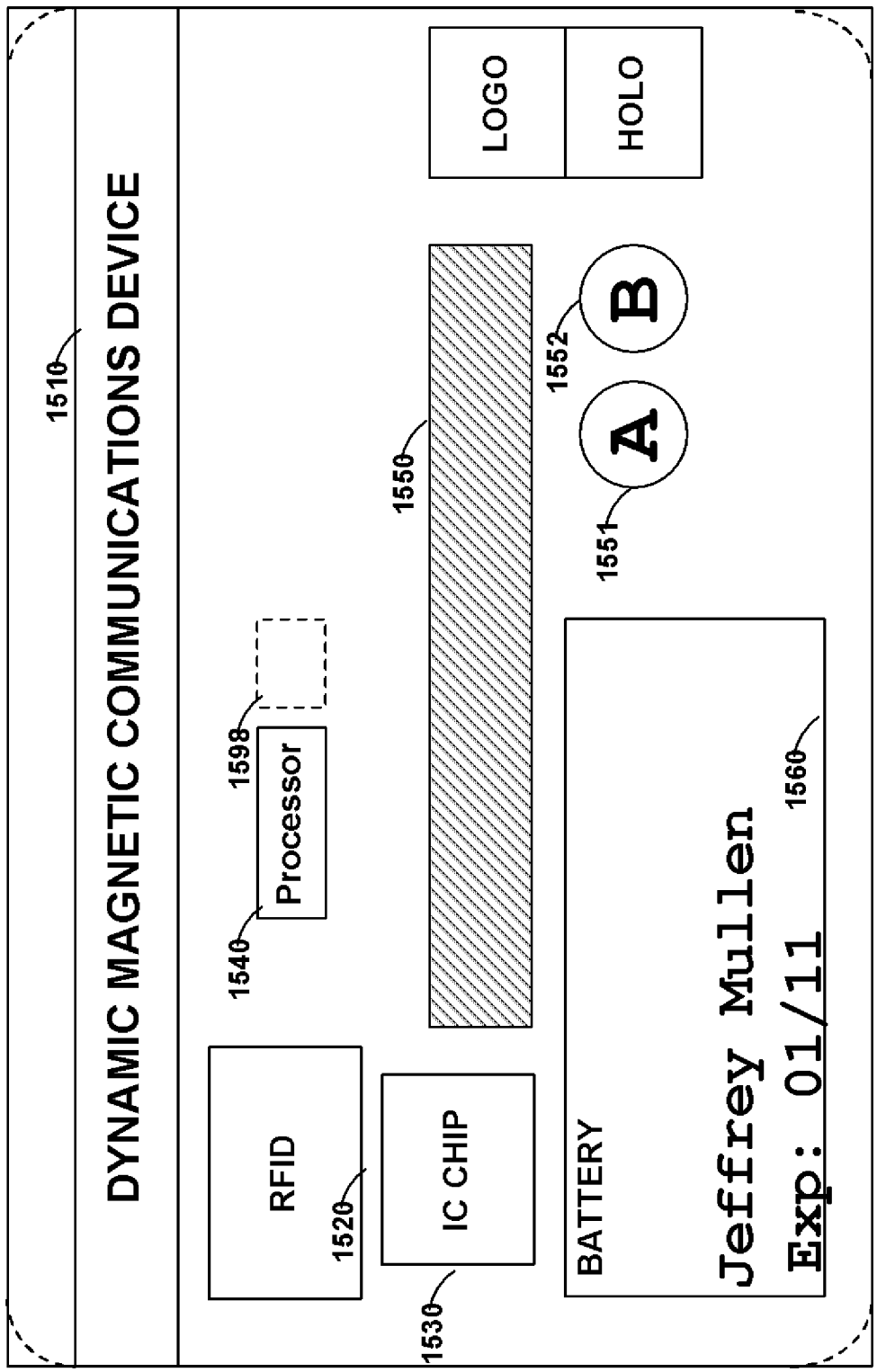
FIG. 15 is an illustration of a card constructed in accordance with the principles of the present invention.

FIG. 15 shows card 1500 that may include, for example, one or more IC chips 1530 (e.g., EMV chips), RFID antennas 1520, processors 1540, displays 1550, dynamic magnetic communications devices 1510 (e.g., magnetic encoders and/or magnetic emulators), batteries 1560, and buttons 1551 and 1552. Additional circuitry 1598 may be provided which may be, for example, one or more oscillators or emulator driving circuits. Persons skilled in the art will appreciate that button 1551 may, for example, be utilized by a user to select one encryption algorithm for a number displayed on display 1550 while button 1552 may be utilized by a user to select a different encryption algorithm. Persons skilled in the art will appreciate that the components of card 1500 may be provided on either surface of a card (e.g., a front or rear surface of the card) or inside of a card. A logo (e.g., of a card issuer) and logo may be provided on either surface of a card.

A button, such as button 1551, may be utilized, for example, to display a number. Such a number may be, for example, encrypted from a secure number based on time or use. For example, one-time use numbers (e.g., a payment number or code) may be retrieved from a list of numbers on memory each time button 1551 is pressed and displayed on display 1550. A processor may only go through each number once on a list. A registration process may be provided in which a user may be requested to enter in a sequence of numbers such that a remote server may validate the card and learn where in a sequence of a list a card currently resides. Numbers may be repeated on a list or may only occur once on a list. All of the numbers available by the length of the number may be utilized by the list or only a portion of the numbers available by the length of the number may be provided by the list. A secret number may be encrypted on a card and a verification server may also have knowledge of this secret number. Accordingly, the remote server may perform the same encryption function as the card on the secret number and verify that the resultant encrypted number is the same as the resultant encrypted number on a card. Alternatively, for example, the remote server may decrypt the received encrypted number to determine the authenticity of the encrypted number and validate an activity (e.g., validate a security access request or a purchase transaction).

Persons skilled in the art will appreciate, for example, that a card may include an IC chip (e.g., EMV chip), RFID, and a dynamic magnetic communications device (e.g., a magnetic emulator or encoder). The same information may be communicated through, for example, any number of such devices (e.g., a dynamic magnetic communications device, RFID, and an EMV chip). A central processor may cause each device to communicate the information (in the same format or a different format). Each component may have its own processor or driving circuitry. Such individual processors or driving circuitry may be coupled to a central processor. An EMV chip may be utilized, for example, to provide control signals to other devices (e.g., circuitry driving a display as well as a dynamic magnetic communications device). Such an EMV chip may receive signals provided by one or more buttons to determine, for example, that a particular button, or sequence of buttons, was pressed by a user.

Persons skilled in the art will appreciate that a read-head housing may include, for example, multiple read-heads. A read-head detector may, more generally, detect a read-head housing and, in doing so, detect a read-head.

Figure 16:
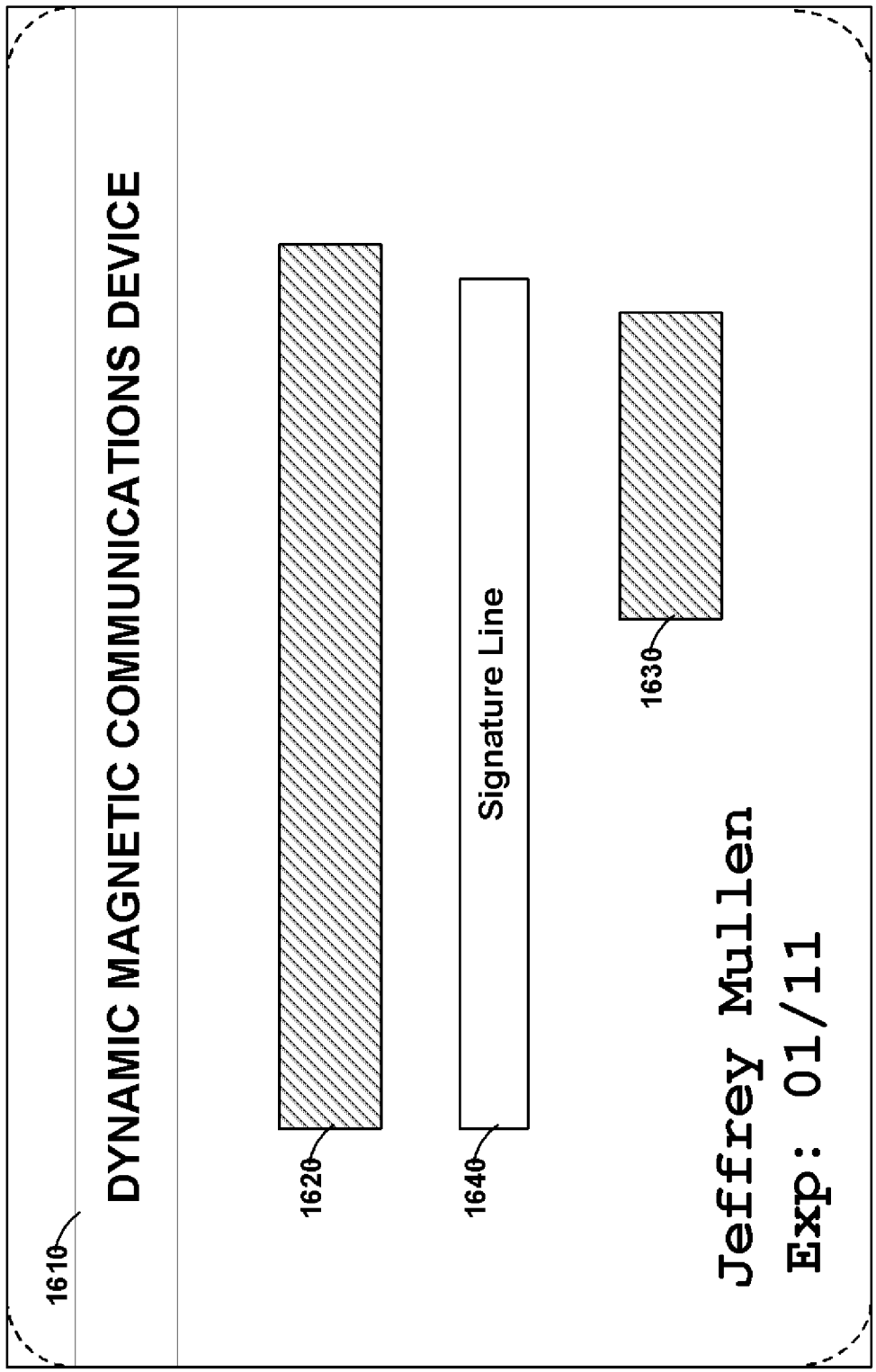
FIG. 16 is an illustration of a card constructed in accordance with the principles of the present invention.

FIG. 16 shows card 1600 that may include, for example, signature area 1640 that may include a material operable to receive marks from a pen (e.g., a signature). Card 1600 may also include, for example, displays 1620 and 1630. Display 1620 may, for example, display a payment number while display 1930 displays a security code (e.g., for online purchase authentication). Display 1620 as well as display 1630 may be utilized on the same side as, for example, dynamic magnetic communications device 1610.

Figure 17:
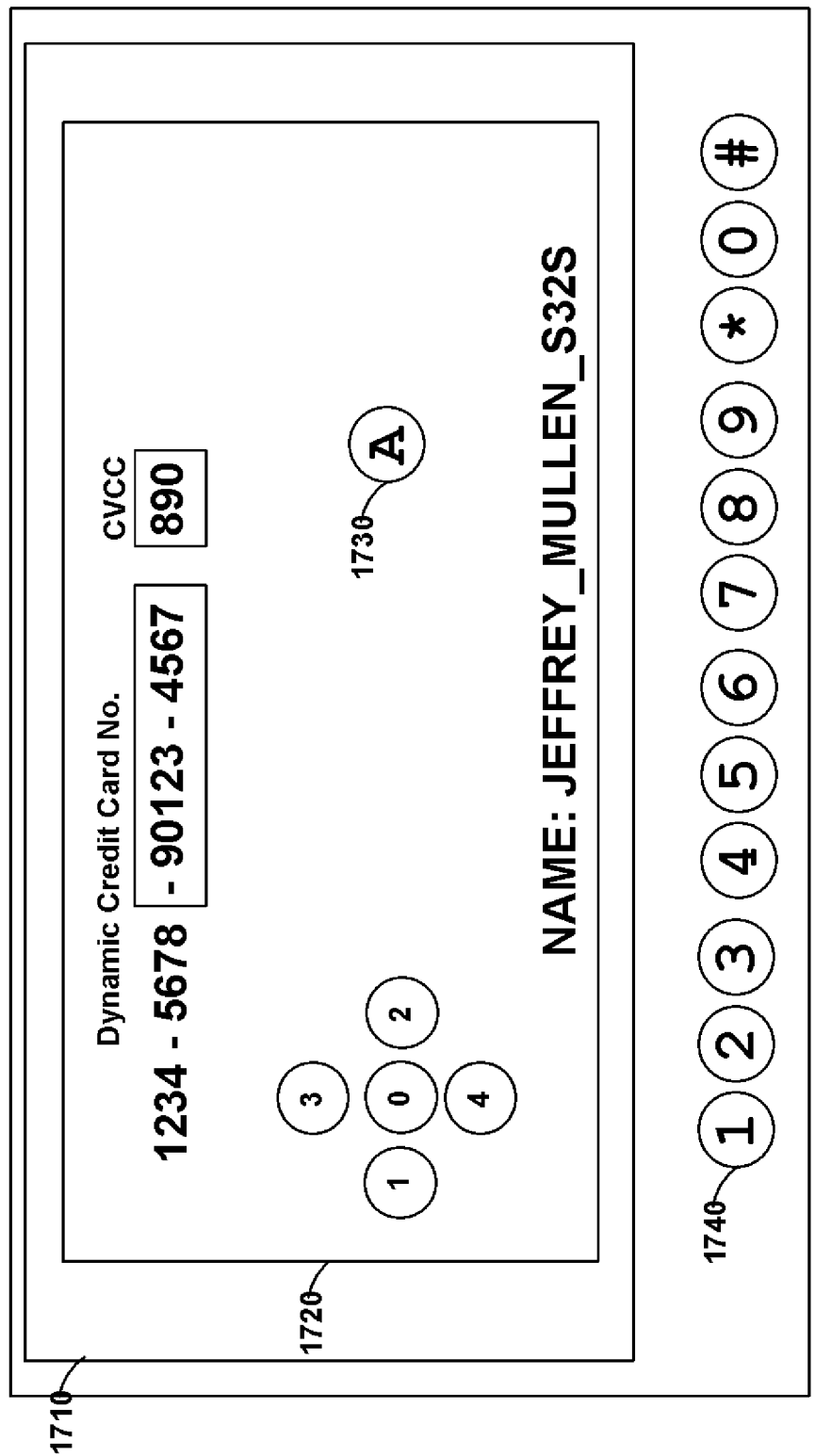
FIG. 17 is an illustration of a card constructed in accordance with the principles of the present invention.

FIG. 17 shows personal electronic device 1700 which may be, for example, a portable telephonic device, portable media player, or any type of electronic device. Persons skilled in the art will appreciate that the functionality of a card may be provided on a personal device and displayed through a graphical user interface. Personal electronic device 1700 may include, for example, user inputs 1740 and display 1710. Virtual card 1720 may be displayed on display 1720. Display 1720 may be a touch-sensitive display such that, for example, virtual button 1230 may be provided on virtual card 1720. Persons skilled in the art will appreciate that cards may be provided as virtual cards and a user may interact with such virtual cards in order to provide a variety of functions. Personal electronic device 1700 may communicate to a card reader such as, for example, an RFID reader.

A display may be bi-stable or non bi-stable. A bi-stable display may consume electrical energy to change the information displayed on the bi-stable display but may not consume electrical energy to maintain the display of that information. A non bi-stable display may consume electrical energy to both change and maintain information on the non bi-stable display. A display driving circuit may be provided, for example, for a bi-stable display (or a non bi-stable display). Such a display driving circuit may step-up a supply voltage (e.g., 1-5 volts) to a larger voltage (e.g., 6-15 volts) such that a bi-stable display may change displayed information. A controller (e.g., a processor) may be utilized to control such a display driving circuit. Persons skilled in the art will appreciate that a display may be configured to display numerical data or alphanumerical data. A display may also be configured to display other indicia (e.g., the image of a battery and its remaining life).

A magnetic stripe reader may, for example, determine information on a magnetic stripe by detecting the frequency of changes in magnetic fields (e.g., flux transversals). A particular frequency of flux transversals may correlate to, for example, a particular information state (e.g., a logic "1" or a logic "0"). Accordingly, for example, a magnetic emulator may change the direction of an electromagnetic field at particular frequencies in order to communicate a different state of information (e.g., a logic "1" or a logic "0").

Persons skilled in the art will appreciate that a magnetic emulator may electromagnetically communicate information serially by changing the magnitude of an electromagnetic field with respect to time. As such, for example, a current in a single direction may be provided through a magnetic emulator in order for that magnetic emulator to generate an electromagnetic field of a single direction and a particular magnitude. The current may then be removed from the magnetic emulator such that, for example, the electromagnetic field is removed. The creation of a presence of an electromagnetic field, and the removal of that electromagnetic field, may be utilized to communicate information to, for example, a magnetic stripe reader. A magnetic stripe reader may be configured to read, for example, the change in flux versus time and may associate an increase in an electromagnetic field (e.g., creation of a field) as one flux transversal and a decrease (e.g., removal of a field) as another transversal. In doing so, for example, driving circuitry (not shown) may be provided which, in turn, controls when current is provided to a magnetic emulator. The timing of magnetic flux transversals, as determined by a magnetic stripe reader, may be utilized by that reader to determine whether a logic one ("1") or logic zero ("0") was communicated. Accordingly, a driving circuit may change the frequency of when current is supplied and removed from a magnetic emulator in order to communicate a logic one ("1") or a logic zero ("0").

A driving circuit may, for example, change the direction of current supplied to a magnetic emulator to increase the amount of change in an electromagnetic field magnitude for a period of time. In doing so, for example, a magnetic stripe reader may more easily be able to discern overall changes in an electromagnetic field and, as such, may more easily be able to discern information. As such, for example, a driving circuit may increase the magnitude of an electromagnetic field by providing negative current, decrease the amount of negative current until no current is provided and provide an increasing positive current in order to provide a large swing in the magnitude of an electromagnetic field. Similarly, a driving circuit may switch from providing one amount of negative current (or positive current) to one amount of positive current (or negative current).

Persons skilled in the art will appreciate that a string of a particular bit of data (e.g., a string of logic zeros "0s") may be communicated before as well as after information is communicated through a magnetic emulator. A magnetic stripe reader may utilize such data, for example, to determine base timing information such that the magnetic stripe reader has a timing reference that the reader can utilize to assist in determining timing changes of perceived flux transversals. Accordingly, for example, a magnetic emulator may send data at different overall frequencies and a magnetic stripe reader may be able to reconfigure itself to receive data at such overall frequencies. Information may be encoded using, for example, Frequency/Double Frequency (F2F) encoding such that magnetic stripe readers may perform, F2F decoding.

A processor may control one or more emulators by, for example, controlling the direction of the current supplied through one or more segments of an emulator. By changing the direction of current through a region, for example, the direction of an electromagnetic field may be changed. Similarly, a processor may control one or more emulators by, for example, controlling the change in magnitude of current supplied through one or more segments of an emulator. As such, for example, a processor may increase the magnitude of current as well as decrease the magnitude of current supplied through an emulator. A processor may control the timing of such increases and decreases in current such that a magnetic emulator may, for example, communicate F2F encoded information.

Persons skilled in the art will appreciate that a dynamic magnetic communications device (e.g., a magnetic emulator or magnetic encoder) may be fabricated, either completely or partially, in silicon and provided as a silicon-based chip. Other circuitry (e.g., driving circuitry) may also be fabricated on such a silicon-based chip. A processor, such as a processor for controlling a magnetic communications device, may be, for example, a programmable processor having on-board programmable non-volatile memory (e.g., FLASH memory), volatile memory (e.g., RAM), as well as a cache. Firmware as well as payment information (e.g., dynamic numbers) may be, for example, communicated from a programming device to a processor's on-board programmable non-volatile memory (e.g., a FLASH memory) such that a card may provide a variety of functionalities. Such a processor may also have one or more power-saving operating modes, in which each operating mode turns OFF a different set of circuitry to provide different levels of power consumption. One or more power-savings modes may turn OFF, for example, one or more clocking circuitry provided on a processor. An Application-Specific Integrated Circuit (ASIC) may also be included in a card or other device to provide, for example, processing, dynamic magnetic communications, as well as driving capabilities.

Persons skilled in the art will also appreciate that the present invention is not limited to only the embodiments described. Instead, the present invention more generally involves dynamic information. Persons skilled in the art will also appreciate that the apparatus of the present invention may be implemented in other ways then those described herein. All such modifications are within the scope of the present invention, which is limited only by the claims that follow.

What is claimed is:

1. A portable device comprising:
   a battery;
   a coupling operable to receive a removable cable to recharge said battery; and
   a magnetic emulator operable to serially communicate a first magnetic stripe data track and a second magnetic stripe data track to a first magnetic stripe data track receiver and a second magnetic stripe data track receiver of a payment card reader while located outside of said payment card reader.

2. The portable device of claim 1, further comprising a display operable to display a virtual payment card, wherein said display is operable to display alphanumeric data.

3. The portable device of claim 2, wherein said display is further operable to display graphical information.

4. The portable device of claim 1, wherein a dynamic code is communicated to said payment card reader and said dynamic code is utilized to validate a purchase transaction.

5. The portable device of claim 1, wherein a dynamic code based on use is communicated to said payment card reader.

6. The portable device of claim 1, wherein a dynamic code based on time is communicated to said payment card reader.

7. The portable device of claim 1, wherein said portable device is a portable telephonic device.

8. The portable device of claim 1, wherein said magnetic emulator is provided on a printed circuit board.

9. The portable device of claim 1, wherein said magnetic emulator is provided on FR4.

10. The portable device of claim 1, further comprising a material operable to reduce the effect of electromagnetic fields.

11. The portable device of claim 1, further comprising a display operable to display a virtual card, wherein said virtual card undergoes a registration process to validate said virtual card.

12. The portable device of claim 1, further comprising a button.

13. The portable device of claim 1, further comprising a display and a button.

14. The portable device of claim 1, wherein said first magnetic stripe data track is F2F encoded.

15. The portable device of claim 1, wherein said first magnetic stripe data track includes a first start sentinel and a first end sentinel and said second magnetic stripe data track includes a second start sentinel and a second end sentinel.

16. The portable device of claim 1, further comprising a processor and switching circuitry operable to control said magnetic emulator.

17. The portable device of claim 1, further comprising a processor and switching circuitry including a transistor operable to control said magnetic emulator.

18. The portable device of claim 1, further comprising switching circuitry coupled to said magnetic emulator.

19. The portable device of claim 1, further comprising switching circuitry coupled to said magnetic emulator, wherein said switching circuitry includes a transistor.

20. The portable device of claim 1, further comprising a plurality of buttons.

21. The portable device of claim 1, wherein a manually entered identification code is utilized to utilize said magnetic emulator.

22. The portable device of claim 1, further comprising a display, wherein a manually entered identification code is utilized to utilize said display.

23. The portable device of claim 1, wherein said removable cable is operable to provide information.

24. The portable device of claim 1, further comprising an RFID antenna,
   wherein said magnetic emulator and said RFID antenna are operable to communicate data to said reader.

25. The portable device of claim 1, wherein said magnetic emulator is operable to communicate with said reader based on positioning of said portable device.

26. The portable device of claim 1, further comprising RFID circuitry operable to detect the presence of an RFID antenna.

* * * * *